United States Patent
Schroer et al.

(10) Patent No.: US 6,274,865 B1
(45) Date of Patent: Aug. 14, 2001

(54) ANALYSIS OF DOWNHOLE OBM-CONTAMINATED FORMATION FLUID

(75) Inventors: Jon J. Schroer, Bear, DE (US); Oliver C. Mullins, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/255,999

(22) Filed: Feb. 23, 1999

(51) Int. Cl.[7] .................................................. G01V 8/02
(52) U.S. Cl. ...................... 250/269.1; 250/255; 250/256
(58) Field of Search ............................... 250/269.1, 262, 250/261, 256, 255

(56) References Cited

U.S. PATENT DOCUMENTS

| | | |
|---|---|---|
| 3,780,575 | 12/1973 | Urbanosky . |
| 3,859,851 | 1/1975 | Urbanosky . |
| 4,860,581 | 8/1989 | Zimmerman et al. . |
| 4,936,139 | 6/1990 | Zimmerman et al. . |
| 4,994,671 | 2/1991 | Safinya et al. . |
| 5,167,149 | 12/1992 | Mullins et al. . |
| 5,201,220 | 4/1993 | Mullins et al. . |
| 5,247,830 | * 9/1993 | Goode ................................ 73/152.51 |
| 5,266,800 | 11/1993 | Mullins . |
| 5,331,156 | 7/1994 | Hines et al. ........................ 250/256 |
| 5,859,430 | 1/1999 | Mullins et al. . |

* cited by examiner

Primary Examiner—Constantine Hannaher
(74) Attorney, Agent, or Firm—William B. Batzer; John L. Lee

(57) ABSTRACT

A method and apparatus is provided for determining OBM filtrate fraction in a downhole fluid sample. One embodiment of the method is used when there is significant difference between the coloration of formation fluid and the coloration of OBM filtrate. Another is used when there is little or no difference between the coloration of formation fluid and the coloration of OBM filtrate. Another determines GOR of formation fluid corrected for OBM filtrate contamination. Another determines OD of formation fluid corrected for OBM filtrate contamination. Another determines conditions that would render optical density measurements invalid and sample capture premature. Another predicts the reduction of filtrate fraction for a specific extended pumping time. Another initiates sample capture when computed contamination fraction exhibits stable asymptotic convergence.

61 Claims, 16 Drawing Sheets

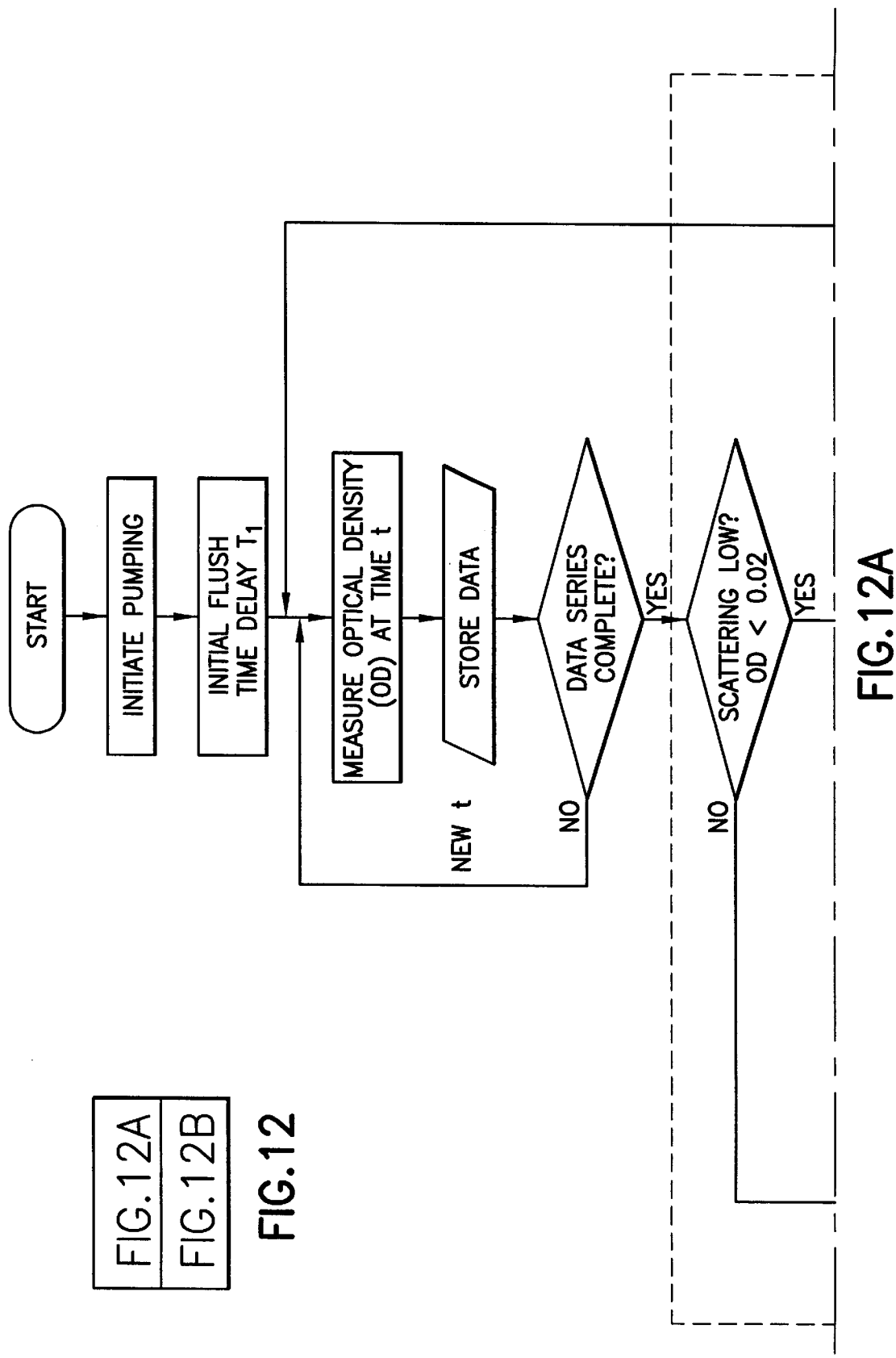

ANALYSIS OF DOWNHOLE OBM-CONTAMINATED FORMATION FLUID

The present invention is related to co-owned U.S. Pat. Nos. 3,780,575 and 3,859,851 to Urbanosky, co-owned U.S. Pat. Nos. 4,860,581 and 4,936,139 to Zimmerman et al., co-owned U.S. Pat. No. 4,994,671 to Safinya et al., and co-owned U.S. Pat. Nos. 5,266,800 and 5,859,430 to Mullins. The invention is also related to co-owned, copending U.S. application Ser. No. 09/015,812, filed Jan. 29, 1998 now U.S. Pat. No. 5,939,717.

TECHNICAL FIELD

The present invention relates to the analysis of downhole fluids in a geological formation. More particularly, the present invention relates to apparatus and methods for downhole optical analysis of formation fluid contaminated by oil based mud filtrate.

BACKGROUND OF THE INVENTION

Schlumberger Technology Corporation, the assignee of this application, has provided a commercially successful borehole tool, the MDT (a trademark of Schlumberger), which extracts and analyzes a flow stream of fluid from a formation in a manner substantially as set forth in co-owned U.S. Pat. Nos. 3,859,851 and 3,780,575 to Urbanosky. The analyzer module of the MDT, the OFA (a trademark of Schlumberger) determines the identity of the fluids in the MDT flow stream. Mullins, in co-owned U.S. Pat. No. 5,266,800, teaches that by monitoring optical absorption spectrum of the fluid samples obtained over time, a real time determination can be made as to whether a formation oil is being obtained as opposed to oil based mud (OBM) filtrate. In particular, the Safinya patent discloses a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly. Prior art equipment is shown in FIGS. 1A–1C.

Because different fluid samples absorb energy differently, the fraction of incident light absorbed per unit of path length in the sample depends on the composition of the sample and the wavelength of the light. Thus, the amount of absorption as a function of the wavelength of the light, hereinafter referred to as the "absorption spectrum", has been used in the past as an indicator of the composition of the sample. For example Safinya, in U.S. Pat. No. 4,994,671, teaches, among other things, that the absorption spectrum in the wavelength range of 0.3 to 2.5 microns can be used to analyze the composition of a fluid containing oil. The disclosed technique fits a plurality of data base spectra related to a plurality of oils and to water, etc., to the obtained absorption spectrum in order to determine the amounts of different oils and water that are present in the sample.

When the desired fluid is identified as flowing in the MDT, sample capture can begin and formation oil can be properly analyzed and quantified by type. Samples are used to determined important fluid properties such as the gas-oil ratio (GOR), saturation pressure, wax and asphaltene precipitation tendency, fluid densities and fluid composition. These parameters help set various production parameters and also relate to the economic value of the reserve.

Prevalent use of oil based mud (OBM) in some markets has resulted in a premium placed on discriminating between OBM filtrate and crude oil. A variety of oils are used as the base for OBM such as diesel, synthetics such as $C16$ and $C18$ monoalkenes, and even crude oil. Due to the variety of base fluids and their overlapping properties with crude oils, it is difficult to identify a single signature of OBM to contrast it with crude oil. Furthermore, the use of a label or taggant for the OBM filtrate is often discouraged in part because of the difficulty in labeling at a fixed concentration 5000 barrels of mud and in part because mud engineers do not want to use any additives which may have an unknown significant consequence on drilling characteristics. Mullins, in U.S. Pat. No. 5,266,800, teaches that by monitoring optical absorption spectrum of the fluid samples obtained over time, a real time determination can be made as to whether a formation oil is being obtained as opposed to OBM filtrate. As noted above, Mullins, in U.S. Pat. No. 5,266,800, discloses how the coloration of crude oils can be represented by a single parameter which varies of several orders of magnitude. The OFA was modified to include particular sensitivity towards the measurement of crude oil coloration, and thus filtrate coloration. During initial extraction of fluid from the formation, OBM filtrate is present in relatively high concentration. Over time, as extraction proceeds, the OBM filtrate fraction declines and crude oil becomes predominant in the MDT flowline. Using coloration, as described in U.S. Pat. No. 5,266,800, this transition from contaminated to uncontaminated flow of crude oil can be monitored.

U.S. Pat. Nos. 3,780,575 and 3,859,851 to Urbanosky, U.S. Pat. Nos. 4,860,581 and 4,936,139 to Zimmerman et al., U.S. Pat. No. 4,994,671 to Safinya et al., and U.S. Pat. Nos. 5,266,800 and 5,859,430 to Mullins are hereby incorporated herein by reference.

SUMMARY OF THE INVENTION

The applicants discovered that the measured optical density of a downhole formation fluid sample contaminated by OBM filtrate changes slowly over time and approaches an asymptotic value corresponding to the true optical density of formation fluid. The applicants also discovered that a calculated gas oil ratio (GOR), derived from measured optical density measurements of a downhole formation fluid sample contaminated by OBM filtrate also changes slowly over time and approaches an asymptotic value corresponding to the true GOR of formation fluid.

The applicants recognized the potential value, in borehole investigative logging, of a real time log of OBM filtrate fraction.

The applicants also discovered that it would be possible to estimate OBM filtrate fraction by measuring optical density values at one or more frequencies, curve fitting to solve for an asymptotic value, and using the asymptotic value to calculate OBM filtrate fraction.

The applicants also discovered that it would be possible, in like manner, to estimate GOR corrected for OBM filtrate fraction, and OD corrected for OBM filtrate fraction.

The applicants also discovered that it would be possible, in like manner, to predict future filtrate fraction as continued pumping flushes the region around the MDT substantially free of OBM filtrate.

The applicants recognized the need to provide appropriate tests to validate, or invalidate, asymptote analysis so as to screen out erroneous measurements caused, for example, by OBM filtrate entering the MDT tool through ineffective mudcake forms.

The applicants further recognized that such estimates would have value not only in boreholes, but also in established wells.

OBJECTS OF THE INVENTION

Therefore it is an object of the invention to provide a method and apparatus for determining oil based mud filtrate fraction in a downhole fluid sample that is contaminated by OBM filtrate.

It is another object of the invention to provide a method and apparatus for determining oil based mud filtrate fraction based on optical density (OD) for use when there is significant difference between the coloration of formation fluid and the coloration of oil based mud filtrate.

It is another object of the invention to provide a method and apparatus for determining oil based mud filtrate fraction based on gas oil ratio (GOR) for use when there is little or no difference between the coloration of formation fluid and the coloration of oil based mud filtrate.

It is another object of the invention to provide a method and apparatus for determining GOR of formation fluid corrected for OBM filtrate contamination.

It is another object of the invention to provide a method and apparatus for determining optical density (OD) of formation fluid corrected for OBM filtrate contamination.

It is another object of the invention to provide a method and apparatus for detecting the presence of particulates in the sample that would render optical density measurements invalid and sample capture premature, either because flushing is not yet complete or because ineffective mudcake forms are allowing continuous inflow of contaminating OBM filtrate.

It is another object of the invention to provide a method and apparatus for predicting the reduction of filtrate fraction for a specific extended pumping time.

It is another object of the invention to provide a method and apparatus for allowing the operator to pre-set specific extended pumping time in accordance with a predicted reduction of filtrate fraction.

It is another object of the invention to provide a method and apparatus for initiating sample capture when computed contamination fraction exhibits stable asymptotic convergence and is below a predetermined value.

Determining OBM Filtrate Fraction from OD/ Coloration

A preferred embodiment of the method for determining OBM filtrate fraction of downhole fluid from measured OD values uses a borehole tool having a pump, a flowline, and an optical analyzer. The method includes pumping downhole fluid through the analyzer; measuring optical density (OD) of downhole fluid to produce a series of OD values at intervals of time; and calculating an OD asymptotic ratio indicative of OBM filtrate fraction. Calculating the OD asymptotic ratio includes solving a first mathematical function for coefficients by fitting the series of OD values to the first mathematical function, then using at least one of the coefficients in a second mathematical function to determine OBM filtrate fraction. The first mathematical function expresses OD as a function of time, the first mathematical function has one coefficient representing an unknown asymptotic value, and at least one term which decreases with time. The first mathematical function is $OD(t)=m_1+m_2 t^{-x}$, in which $m_1$ is a first coefficient representing the unknown OD asymptotic value, $m_2$ is a second coefficient, and x is a selected decay value, approximately 0.5, and within the range 0.2 to 0.8. The second mathematical function is Fraction=$(m_1-OD)/m_1$, or Fraction=$|(m_1-OD)|/m_1$, in which ml is an OD asymptotic value determined by solving for coefficients, and OD is an OD value derived from the series of OD values. Measuring OD includes illuminating downhole fluid with light of wavelength in the visible spectrum selected in accordance with coloration contrast between formation fluid and OBM filtrate. The wavelength is selected as being the shortest wavelength that yields an OD in the range 0.05 to 2.0. The first wavelength selected is approximately $537 \times 10^{-9}$m (537nm).

Alternatively, the wavelength is selected in accordance with contrast between the OD of condensate dissolved in the formation fluid and the OD of OBM filtrate, and is proximate to a methane peak, and on a lower wavelength shoulder of the methane peak. The preferred embodiment includes validating the calculated asymptotic ratio by testing for scattering at wavelength 1600nm, to determine if OD is less than 0.02. The preferred embodiment also includes validating the calculated asymptotic ratio by testing for monotonically changing OD values, indicative of color change with time, to verify asymptotic convergence of OD values, including testing for $m_2<1$ or $|m_2|<1$. The preferred embodiment also includes validating the calculated asymptotic ratio by repeating the steps needed to produce a series of asymptotic values; and testing the series of asymptotic values for stability by testing for $(m_1-m_{1prev.})/m_1<0.05$ or $|(m_1-m_{1prev.})|/m_1<0.05$.

Determining OBM Filtrate Fraction from OD/GOR

A preferred embodiment of the method for determining OBM filtrate fraction of downhole fluid from calculated GOR values uses a borehole tool having a pump, a flowline, and an optical analyzer. The method includes pumping downhole fluid through the analyzer; illuminating the downhole fluid with light in the visible spectrum and with near infra-red (NIR) light at a wavelength associated with gas; detecting optical absorbance in the visible spectrum to produce a visible spectrum optical density value and NIR absorbance to produce an NIR optical density value; calculating gas oil ratio (GOR) as the ratio of the NIR optical density value to the visible spectrum optical density value; repeating steps a) to d) to produce a series of GOR values at intervals of time; and calculating a GOR asymptotic ratio indicative of OBM filtrate fraction. Calculating the GOR asymptotic ratio includes solving a third mathematical function for its coefficients by fitting the series of OD values to the third mathematical function, then using at least one of the coefficients in a fourth mathematical function to determine OBM filtrate fraction. The third mathematical function expresses GOR as a function of time, having one constant coefficient representing an unknown asymptotic value, and at least one term which decreases with time. The third mathematical function includes $GOR(t)=r_1+r_2 t^{-y}$, in which $r_1$ is a first constant coefficient representing the unknown GOR asymptotic value, $r_2$ is a second constant coefficient, and y is a selected decay value of approximately 0.5 and within the range 0.2 to 0.8. The fourth mathematical function includes Fraction $=(r_1-OD)/r_1$, in which $r_1$ is the asymptotic value determined by solving for coefficients, and GOR is a GOR value derived from the series of GOR values.

Determining GOR Corrected for OBM Filtrate Fraction

A preferred embodiment of the method for determining gas oil ratio (GOR) of formation fluid corrected for OBM filtrate contamination includes producing a series of GOR values at intervals of time, and calculating a GOR asymptotic value by fitting the series of GOR values to the above-mentioned third mathematical function.

Determining OD Corrected for OBM Filtrate Fraction

A preferred embodiment of the method for determining optical density (OD) of formation fluid corrected for OBM filtrate contamination includes producing a series of OD values at intervals of time, and calculating an OD asymptotic value by fitting the series of OD values to the above-mentioned first mathematical function.

Validating Initiation of Sample Capture

A preferred embodiment of the method for validating initiation of sample capture of downhole fluid, uses a borehole tool having a pump, a flowline, an optical analyzer, and means for capturing a sample; the pump pumping downhole fluid through the analyzer.

The method further includes measuring optical density (OD) of downhole fluid, at a wavelength of approximately $1600 \times 10^{-9}$m (1600nm) to test for scattering; and testing for OD less than 0.02.

The method further includes measuring optical density (OD) of downhole fluid produce a series of optical density values at intervals of time; calculating an asymptotic value indicative of optical density of formation fluid from the series of optical density values; repeating the steps needed to produce a series of asymptotic values; and testing for asymptotic values monotonicaly changing at less than a predetermined rate.

Predicting OBM Filtrate Fraction after Further Pumping

A preferred embodiment of the method for predicting OBM filtrate fraction of downhole fluid after a predefined second period of pumping, uses a borehole tool having a pump, a flowline, and an optical analyzer. The method includes pumping downhole fluid through the analyzer; illuminating the downhole fluid with light in the visible spectrum and with near infra-red (NIR) light at a wavelength associated with gas; detecting optical absorbance in the visible spectrum to produce a visible spectrum optical density value and NIR absorbance to produce NIR optical density value; calculating GOR as the ratio of the NIR optical density value to the visible spectrum optical density value; repeating during a first period of pumping the steps needed to produce a series of GOR values at intervals of time; fitting the series of ratio values to a mathematical function of the form $GOR(t) = r_1 + r_2 t^{-Y}$, in which $r_1$ is the unknown asymptotic value, $r_2$ is a constant, and y is a selected decay value, to solve for $r_1$ and $r_2$; and solving equation FRACTION $= [r_2 T_{Pm}^{-y}]/r_1$, where $T_{Pm}$ is the predefined second period of pumping.

Apparatus

A preferred embodiment of the borehole apparatus of the present invention includes a borehole tool including a flowline with an optical cell, a pump coupled to the flowline for pumping downhole fluid through the cell, and an analyzer optically coupled to the cell, the analyzer configured to produce OD values; and control means for accepting OD values and calculating therefrom an asymptotic value.

In one embodiment the asymptotic value is an OD asymptotic value indicative of OBM filtrate fraction.

In another embodiment the asymptotic value is a GOR asymptotic ratio indicative of OBM filtrate fraction.

In another embodiment the asymptotic value is a GOR asymptotic value indicative of GOR corrected for OBM filtrate fraction.

In another embodiment the asymptotic value is a GOR asymptotic value indicative of GOR corrected for OBM filtrate fraction.

In another embodiment the asymptotic value is an OD asymptotic value indicative of OD corrected for OBM filtrate fraction.

In another embodiment the control means further includes means for testing OD values to validate measurement by confirming asymptotic convergence.

In another embodiment the control means further includes means for testing OD values to validate measurement by confirming stable asymptote.

In another embodiment the asymptotic value is an OD asymptotic value indicative of OBM filtrate fraction after a selected additional pumping time.

Stored Program

A preferred embodiment of the stored program of the present invention includes a computer usable medium having computer readable program code thereon, the medium adapted for use with borehole apparatus, the program code including code structured to accept a series of OD values and to calculate from the OD values an asymptotic value indicative of OBM filtrate fraction, an asymptotic value indicative of GOR of formation fluid and an asymptotic value indicative of OD of formation fluid.

DETAILED DESCRIPTION OF THE INVENTION

The present invention is applicable to both borehole investigative logging and to production logging. For purposes of brevity, the description herein will be primarily directed to borehole investigative logging, and the terms "borehole" and "borehole tool" should be read throughout the specification and claims to encompass a (cased) well and a tool used in a well, as well as in a borehole.

Figure 1A:
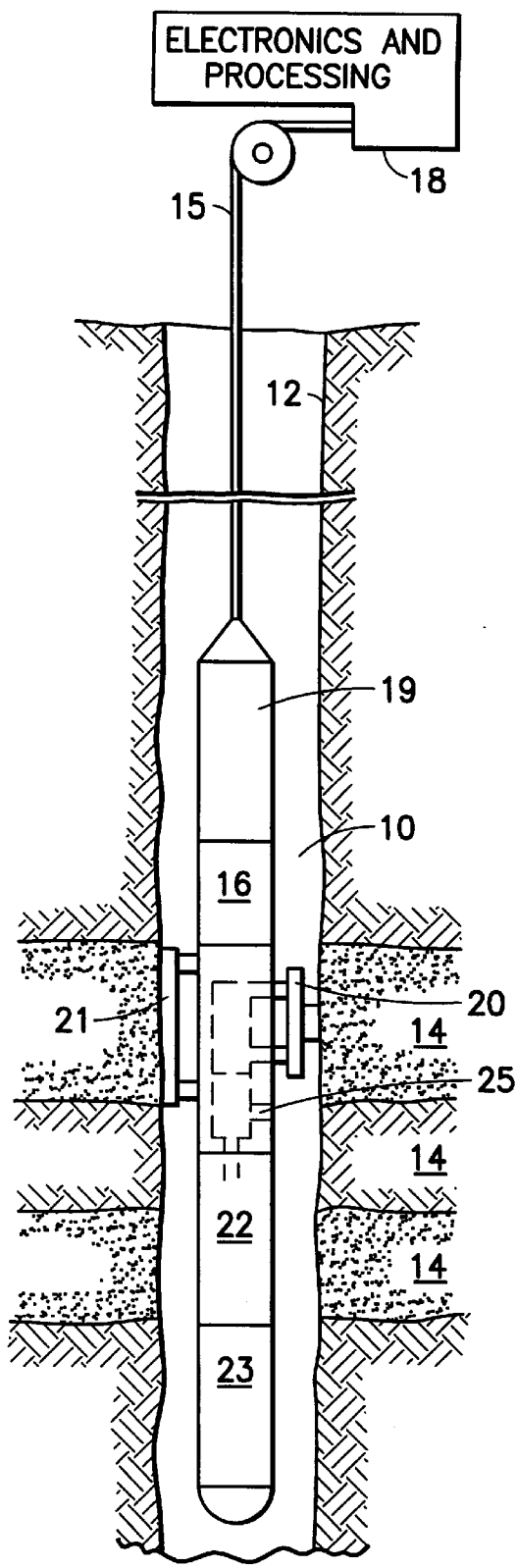
FIG. 1A (prior art) is a schematic diagram of a borehole apparatus for analyzing borehole fluids.

FIG. 1A (prior art) is a schematic diagram of a borehole apparatus similar to the borehole apparatus of the present invention. Borehole tool 10, as shown in FIG. 1A, is the tool for testing earth formation and analyzing the composition of fluids from the formation 14 described in U.S. Pat. No. 4,994,671 to Safinya. As illustrated, tool 10 is suspended in borehole 12 from the lower end of a typical multiconductor cable 15 that is spooled in the usual fashion on a suitable winch (not shown) on the formation surface. On the surface, cable 15 is preferably electrically coupled to electrical control system 18. The tool 10 includes an elongated body 19 which encloses the downhole portion of tool control system 16. Elongated body 19 also carries a selectively extendible fluid admitting assembly 20 and a selectively extendible tool anchoring member 21 which are respectively arranged on opposite sides of the body. Fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18. The apparatus of the present invention differs from that disclosed by Safinya et al. in that electrical control system 18 of the present invention includes processor capability with additional functional capabilities in respect to determination of asymptotic values. The apparatus of present invention in its various embodiments includes "control means" whose functions may be provided by a processor adjunct to, or a processor included within a modified version of the Safinya electrical control system 18 with multiconductor cable 15.

Figure 1B:
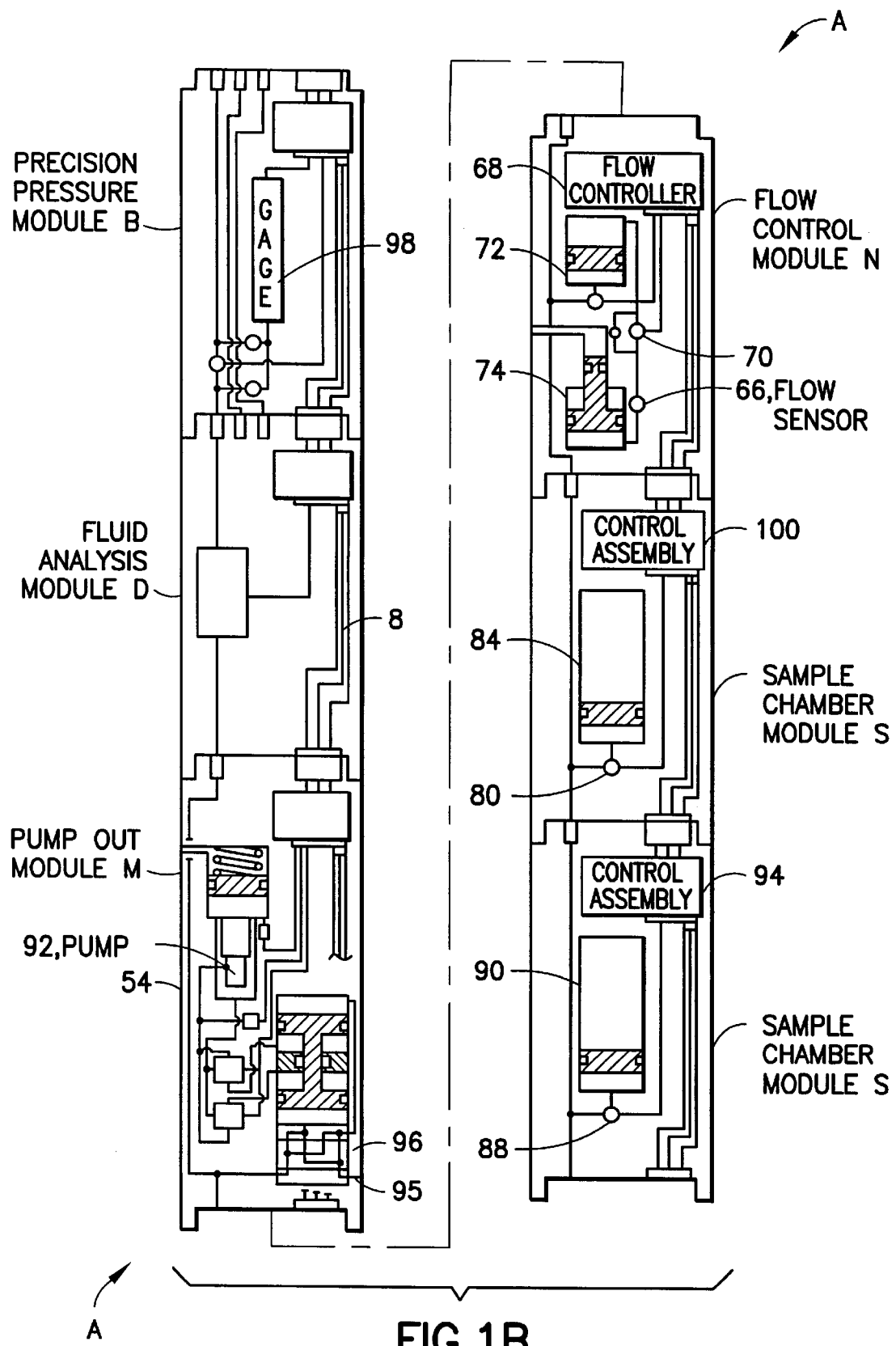
FIG. 1B (prior art) is a schematic diagram of the borehole tool of FIG. 1A.

FIG. 1B (prior art) shows further detail of the borehole tool of FIG. 1A. The tool includes pump out module M with its flowline 54 and its pump 92; fluid analysis module D; and sample chamber modules S. A full description of these items can be found in U.S. Pat. No. 4,936,139 to Zimmerman.

Figure 1C:
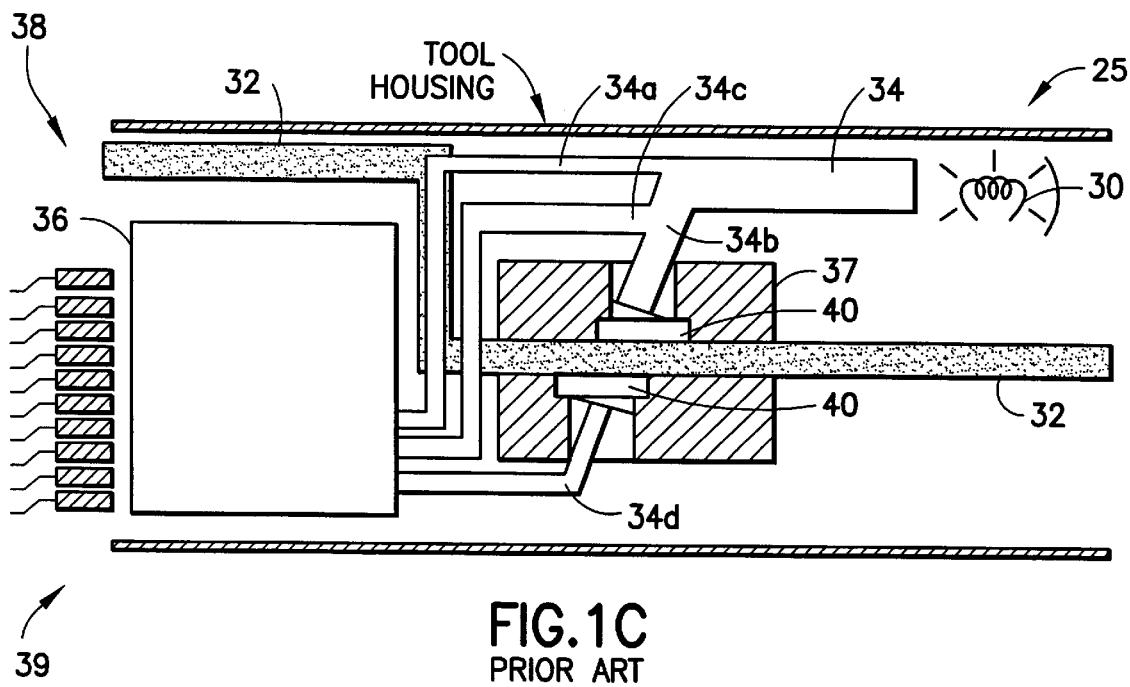
FIG. 1C (prior art) is a schematic diagram of the analyzer of FIG. 1A.

FIG. 1C (prior art) shows further detail of the analyzer housed in module D of FIG. 1B. The analyzer of FIG. 1C is of a type suitable for use in the present invention. The analyzer is described more fully in U.S. Pat. No. 4,994,671 to Safinya. However, the analyzer is configured, and its outputs are used in the present invention in accordance with the novel methods listed below. These methods are different from the methods disclosed by Safina.

The analyzer of present invention preferably has ten channels with wavelengths/wave numbers as follows:

TABLE 1

| Channel Number | Wavelength | Wave Number |
|---|---|---|
| 0 | $476 * 10^{-9}$ m (476 nm) | $4.16 * 10^{-19}$ J (21008 cm$^{-1}$) |
| 1 | $537 * 10^{-9}$ m (537 nm) | $3.69 * 10^{-19}$ J (18622 cm$^{-1}$) |
| 2 | $647 * 10^{-9}$ m (647 nm) | $3.07 * 10^{-19}$ J (15456 cm$^{-1}$) |
| 3 | $815 * 10^{-9}$ m (815 nm) | $2.43 * 10^{-19}$ J (12270 cm$^{-1}$) |
| 4 | $1070 * 10^{-9}$ m (1070 nm) | $1.85 * 10^{-19}$ J (9346 cm$^{-1}$) |
| 5 | $1290 * 10^{-9}$ m (1290 nm) | $1.54 * 10^{-19}$ J (7752 cm$^{-1}$) |
| 6 | $1445 * 10^{-9}$ m (1445 nm) | $1.37 * 10^{-19}$ J (6920 cm$^{-1}$) |
| 7 | $1600 * 10^{-9}$ m (1600 nm) | $1.24 * 10^{-19}$ J (6250 cm$^{-1}$) |
| 8 | $1725 * 10^{-9}$ m (1725 nm) | $1.15 * 10^{-19}$ J (5797 cm$^{-1}$) |
| 9 | $1930 * 10^{-9}$ m (1930 nm) | $1.02 * 10^{-19}$ J (5180 cm$^{-1}$) |

The methods of the present invention use the concept of OBM filtrate fraction decreasing asymptotically over time, coupled with either coloration measurement of optical density, or near-infrared (NIR) measurement of gas oil ratio (GOR), or both, to distinguish between formation oil and OBM filtrate.

Figure 3:
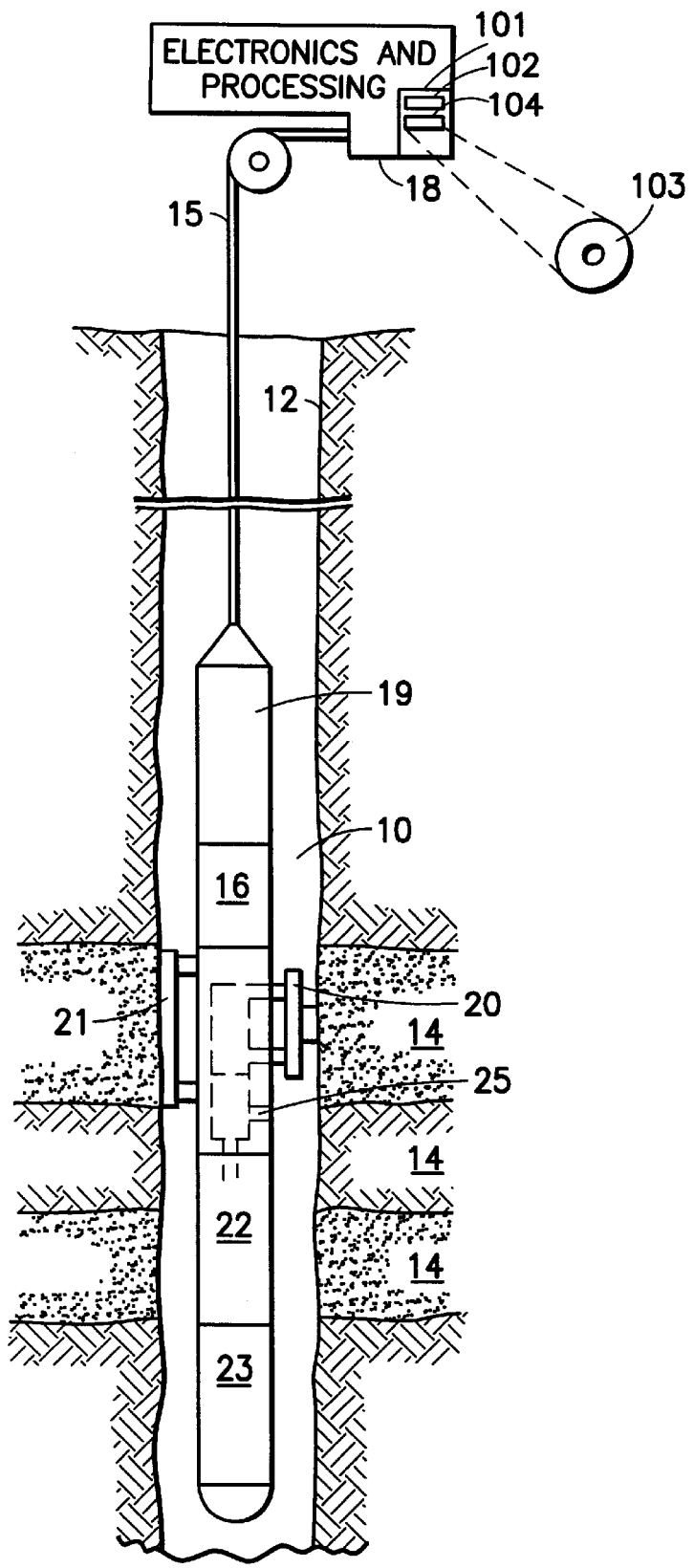
FIG. 3 a schematic diagram of a preferred embodiment of the borehole apparatus of the present invention for analyzing borehole fluids.

The methods of the present invention are preferably embodied in a computer program that runs in a processor 101 located in the protected Electronics and Processing are 18 as shown in FIG. 3. In use, the program is coupled to receive measurement data from analysis module 25 via cable and to deliver control signals to operative elements of the borehole tool 10. As shown in FIG. 3, the computer program may be stored on a computer usable storage medium 102 internal to processor 101, or may be stored on an external computer usable storage medium 103, and electronically coupled to processor 101 for use as needed. In FIG. 3, storage medium 103 is shown as a magnetic disk, fitting into disk drive 104, but it could be an optically readable CD-ROM or a readable device of any other kind, including a remote storage device coupled over a switched telecommunication link.

Real Time Display of OBM OFA Log

Figure 5:
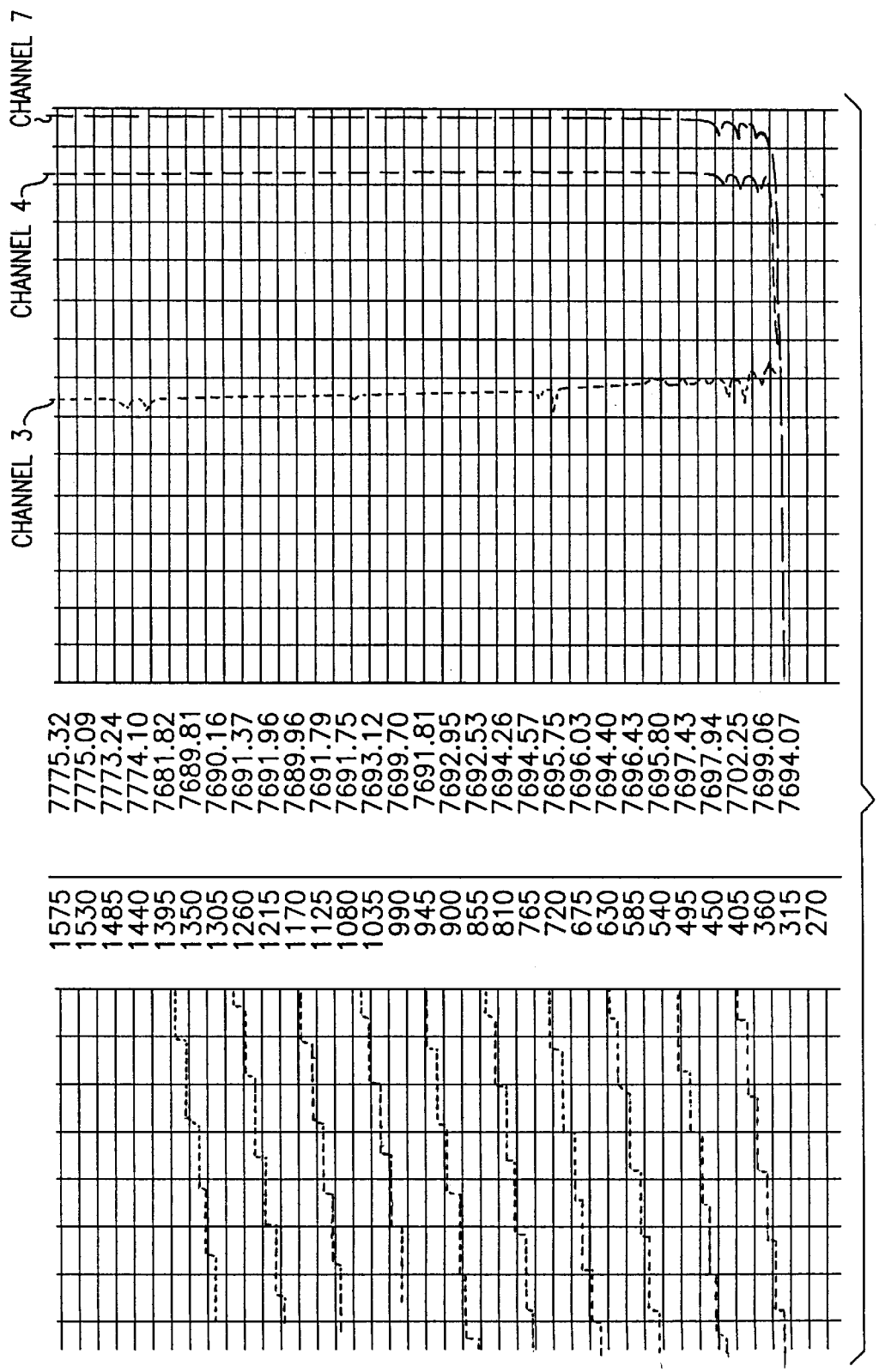
FIG. 5 shows asymptotic behavior in a typical OFA log.
Figure 6:
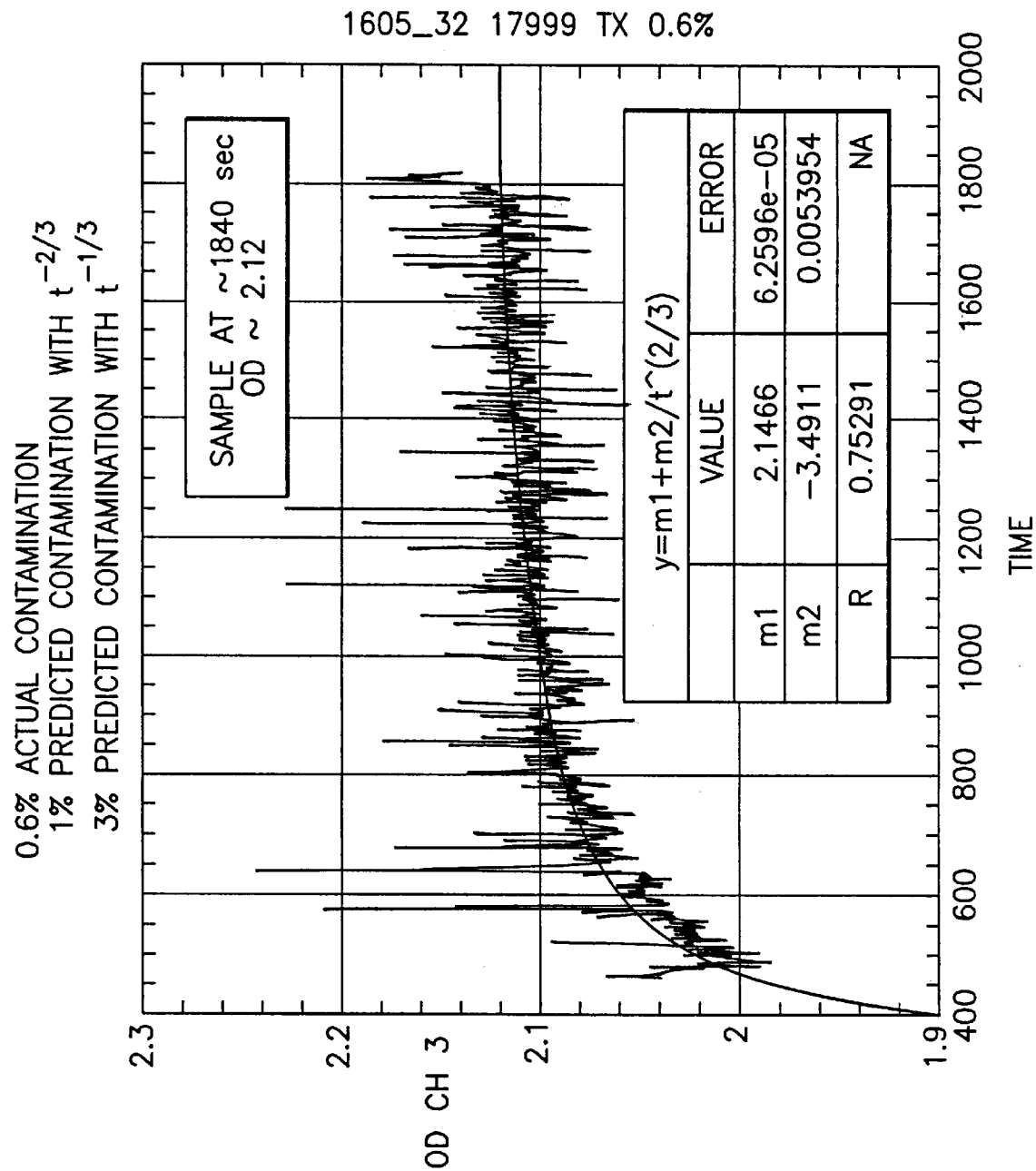
FIG. 6 displays test results of OBM filtrate contaminating measurement.

The applicants recognized the potential value, in borehole investigative logging, of a real time log of OBM filtrate contamination fraction, i.e. percent of contamination. FIG. 5 shows a typical OBM OFA log. The OD of channel 3 is seen to slowly increase as elapsed time increases. Initially the increase is rapid and at later times the increase is slower. This increase is attributed to the reduction of contamination levels in the MDT flowline. Initially, the OBM filtrate contamination is relatively high. Because the filtrate is light in color, the OD of channel 3 (a color channel at 815 nm) is somewhat reduced. As the fraction of (dark) crude oil increases, the OD of channel 3 also increase.

Determining OBM Filtrate Fraction from an OD Asymptote

FIG. 5 shows that the increase in the OD of channel 3 is well behaved and smooth. The curve has the appearance of an asymptotic approach to some unknown final coloration. This curve is typical and is found in most $^{-9}$m OBM OFA logs. We can quantify the contamination by fitting the time evolution curve of the OD of channel 3 with a suitable mathematical function. This function will give the asymptotic or infinite time value of the coloration. This value corresponds to the coloration of pure crude oil. Once this value is known, we employ the assumption that the filtrate is colorless in this channel. With this assumption, we immediately obtain the contamination level by determining the fractional distance of the OD of channel 3 from the asymptotic value. For example, if the OD in channel 3 is 12% below the asymptotic value, then the OBM filtrate contamination in the flowline is 12%. For the best fitting results, select the longest wavelength color channel for which there is significant nonzero OD. This channel selection can easily be automated. In the event that the flowline coloration is too light to make the assumption that the crude oil color is much greater than the OBM filtrate color, then we could use a GOR asymptote instead of an OD asymptote.

Using Coloration to Distinguish Filtrate from Crude Oil

When the contrast in optical density due to coloration, between OBM filtrate and crude oil, is large, it is best to use optical density (OD) to distinguish OBM filtrate from crude oil. Since the OBM filtrates in the Gulf of Mexico tend to be lightly colored, the contrast of optical density due to coloration is greatest for black oils and least for condensates. (Note that gas is separately identified by the OFA in the gas detector so even though gas possesses no color, the OFA has no problem differentiating gas from OBM filtrate.)

A Note on Coloration Absorption Mechanisms

Figure 2:
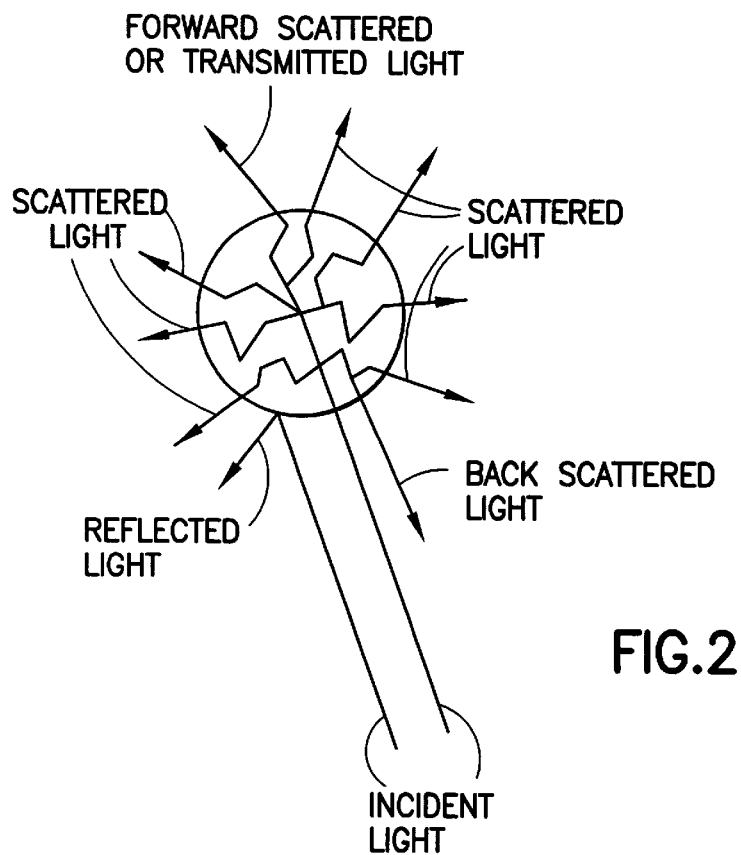
FIG. 2 illustrates scattering paths in an analyzer such as the analyzer of FIG. 1A.

As seen in FIG. 2, several different interactions may occur when light strikes a sample. Typically, if the sample is fluid, some light is reflected at the boundary of the sample while the rest of the light enters the sample. Inside the sample, light is scattered by molecular excitations (Raman scattering) and by collective modes of the medium (e.g., Rayleigh scattering). In general, only a very small fraction of the light is scattered per centimeter of path by the Raman scattering processes. Furthermore, the effects of Rayleigh scattering or other optical scattering processes are usually negligible when the sample to be analyzed is a single phase (e.g. not an emulsion and no suspended solids). So in most cases, most of the light is absorbed. The absorption mechanisms of interest for the present invention include the electronic absorption which relates to the excitation of electronic transitions in aromatic molecules in the fluid such as asphaltenes, resins, and porphyrins; not the vibrational absorption which results from the excitation of overtones of molecular vibrations involving hydrogen atoms.

Selecting the Mathematical Function

Figure 8:
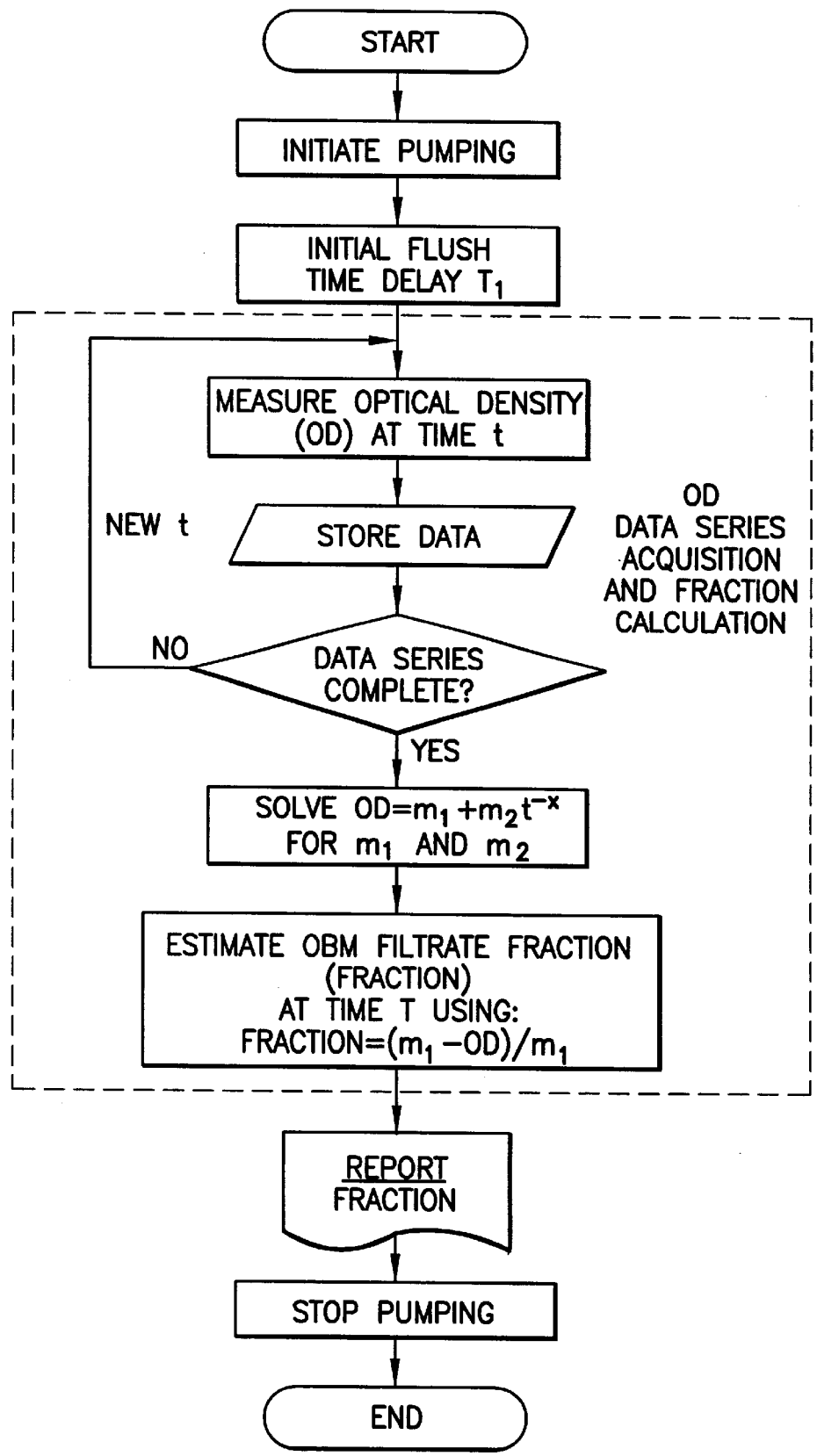
FIG. 8 is a flowchart for a first method of estimating OBM filtrate fraction of downhole fluid—using OD measurements.

A variety of mathematical functions may be used to fit the OD time evolution curve of channel 3. FIG. 8 illustrates a first preferred method of estimating OBM filtrate. The steps of FIG. 8 include making a series of OD measurements, using coloration to distinguish OBM filtrate from crude oil, Eq. 1, and Eq. 2.

Preferably, the form of Eq. 1 is as follows.

$$OD(t) = m_1 + m_2 t^{-x} \qquad \text{Eq. 1}$$

In Eq. 1, $m_1$ is the unknown asymptotic value, $m_2$ is a constant, and x is a selected decay value having a preferred value of approximately 0.5, usually within a range of approximately 0.2 to 0.8, and rarely above 1.0.

The optimal value of x, for use at a given depth in a given bore hole, depends on the (local) extent of invasion of the formation by OBM. For shallow invasion, e.g. because of local presence of lower permeability rock, a lower value of x would be more suitable, for example $x=\frac{1}{3}$. For deep invasion, e.g. because of local presence of higher permeability rock, a higher value would be more suitable, for example $x=\frac{2}{3}$.

It is desirable to minimize pumping time when the tool is stationary in the bore hole because the longer the tool is stationary, the more likely it is to get stuck. It is usually too risky to allow a tool to remain stationary for more than one hour. When a tool gets stuck it is lost—at a cost of approximately $1M. However, it is necessary to allow sufficient pumping time for the log to stabilize and converge. For this reason, the value of x is set to allow stabilization of convergence within about 1/2 hour (1800 seconds) of pumping time. Convergence is deemed to have stabilized when (a) measurements of contamination fraction are monotonically decreasing and (b) the difference between successive measurements is consistently less than a predetermined value, in a preferred embodiment less than 0.1.

After the asymptotic limit has been determined, the OBM contamination filtrate fraction is calculated and listed on the log.

OBM filtrate fraction is calculated using Eq. 2.

$$\text{Fraction} = (m_1 - OD)/m_1 \qquad \text{Eq. 2.}$$

In Eq. 2, $m_1$ is an OD asymptotic value determined by solving Eq. 1 for coefficients, and OD is an OD value derived from the series of OD values.

As time progresses, the fitting is continued. A robust result is obtained only after the asymptotic fit value stabilizes. The stabilized contamination fraction, along with other considerations, can be used to determine when to sample.

As an alternative to Eq. 1, Eq. 1A can be used. Note that Eq. 1A includes at least one exponential term and a constant offset.

$$OD_i(t) = C_1 \exp(-C_2 t) + C_3 \exp(-C_4 t) + C_5 \qquad \text{Eq. 1A}$$

In Eq. 1A, the first exponential term fits the early time behavior, the second exponential term fits the late time behavior, and the constant $C_5$ gives the asymptotic limit which is the parameter of interest. Although this function has variables perhaps making the fitting somewhat problematic, one may be able to reduce the number of parameters by making simplifying assumptions because we are concerned only with the estimation of $C_5$, but not the other parameters.

Curve Fitting

Curve fitting to solve Eq. 1 is preferably performed using the Least Squares Fitting method as detailed in "Data Reduction and Error Analysis for the Physical Sciences", Phillip R. Bevington, McGraw Hill, N.Y., 1969, and specifically as implemented in the Kaleidagraph™, a trademarked software package marketed by Synergy Software of Reading, Pa.

Experimental Results

Figure 7:
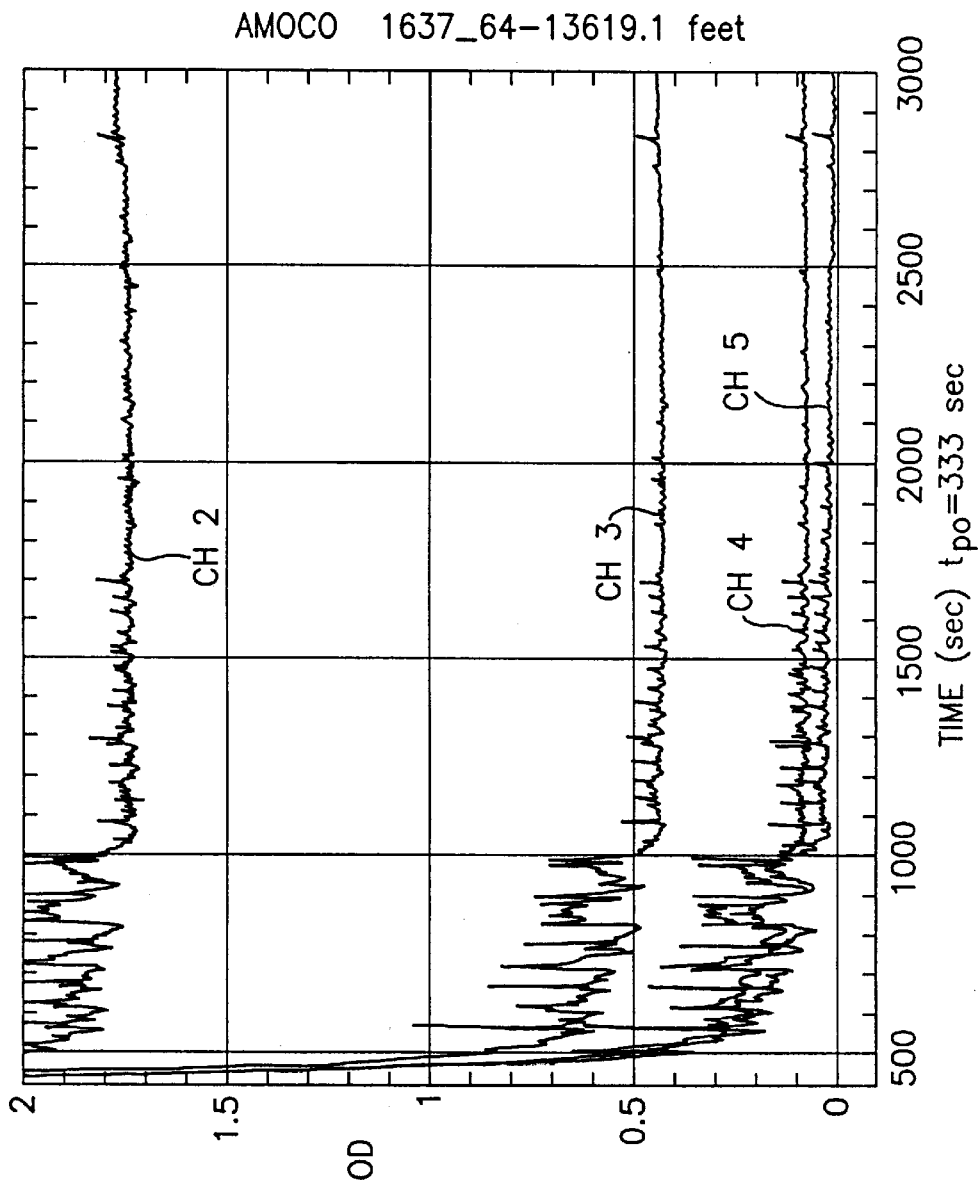
FIG. 7 shows measurement disqualification artifacts.

Experimental results using Eq. 1 with $x=\frac{2}{3}$ and $x=\frac{1}{3}$ are displayed in FIG. 7.

Using NIR-GOR to Distinguish Filtrate from Crude Oil

When the contrast in coloration is large, it is better to distinguish OBM Filtrate from Crude Oil by OD, as described above. When the contrast in coloration is small, it is better to distinguish OBM Filtrate from Crude Oil by NIR-GOR. (If OD>1, use coloration. If OD<1, use NIR-GOR).

Crude oils are classified according to their GOR as follows: Black oils, GOR<2000; Volatile oils, 2000<GOR<3300; Gas condensates, GOR>3300. (Crude oil classifications are customarily stated as standard cubic feet of gas divided by barrels of stock tank oil, scf/bbl, e.g. 2000 scf/bbl and 3300 scf/bbl. In SI units 2000 scf/bbl is 356 m³/m³ and 3300 scf/bbl is 588 m³/m³). The exact value of the thresholds might differ depending on region or investigator being queried. Nevertheless, the concepts are the same. There is an anticorrelation of the gas fraction with the heavy ends, asphaltenes and resins. Thus black oils are characterized by low gas fractions, i.e. small GOR. In contrast with both of these "live oils", which contain at least some gas condensates, OBM filtrate has none, so the GOR of OBM filtrate is always effectively zero.

Figure 4:
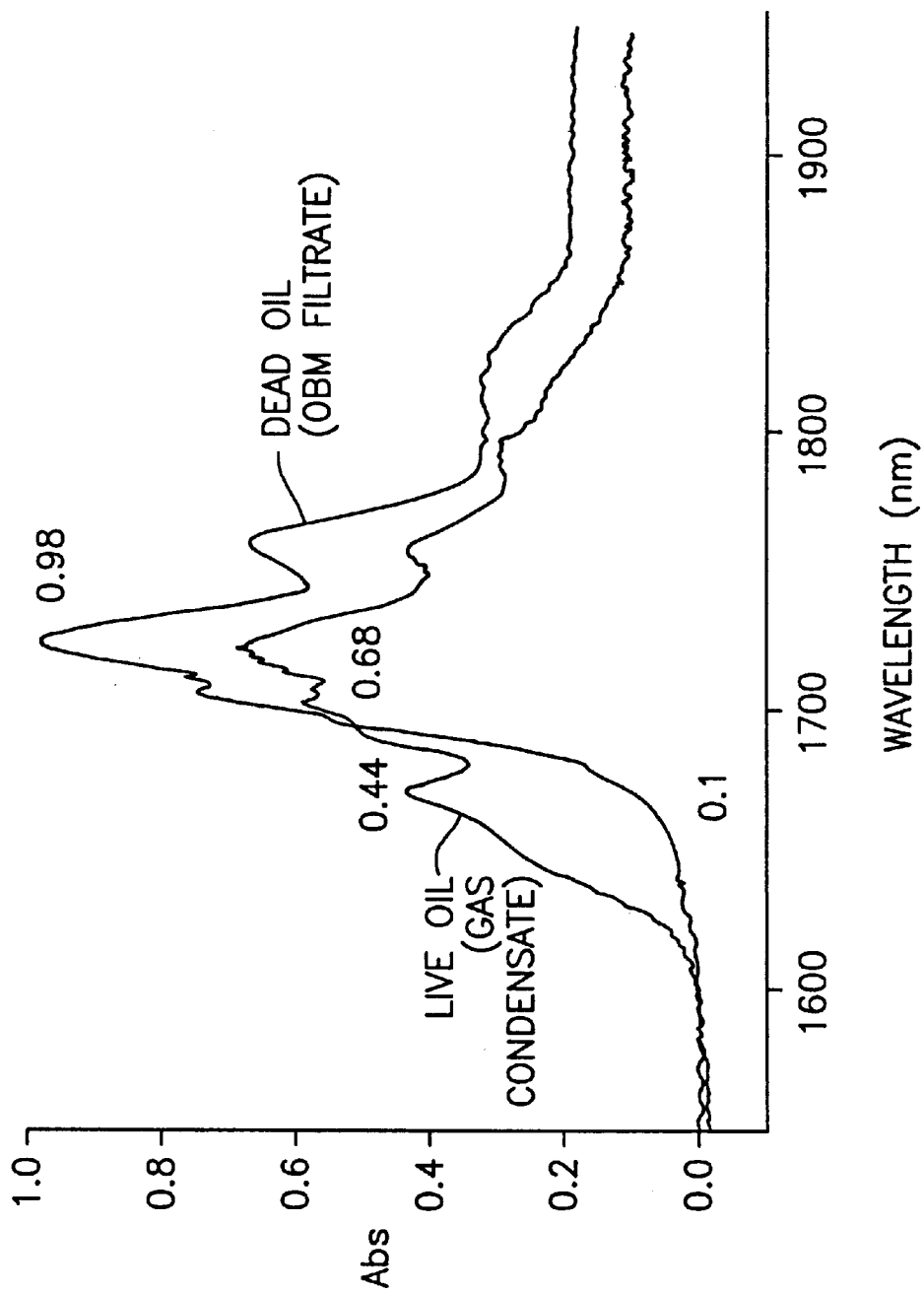
FIG. 4 shows the optical absorption of live oil with its methane peak, and the optical absorption of dead oil—dead oil corresponding to OBM filtrate.

The NIR measurement of GOR relies on making separate measurements of a methane peak such as at $1670\times10^{-9}$m (1670nm) and an oil (—$CH_2$—) peak such as at $1725\times10^{-9}$m (1725nm). FIG. 4 shows the contrasting spectra of a live oil (in this case a gas condensate) vs dead oil (corresponding to a typical OBM filtrate). The OBM filtrate spectrum is nearly identical to that of a dead crude oil. Indeed, if OBM filtrate had a much different NIR spectrum than a dead oil, this difference could be used for discriminating between these two fluids. The contrast depicted in FIG. 4 is due to the high methane fraction in the condensate. This high methane fraction yields a large methane peak (optical density (OD)= 0.44 in FIG. 4). The high methane fraction also dilutes the liquid oil phase thereby substantially reducing the oil peak (OD=0.68 in FIG. 4). The ratio of OD's for the methane vs. oil peak regions is 0.65 for the condensate and 0.01 for the OBM filtrate. This large spectral contrast can be utilized in the same way as coloration. This spectral contrast due to GOR differences, along with time correlation, can be used to distinguish between different levels of contamination of OBM filtrate in a gas condensate.

Figure 9:
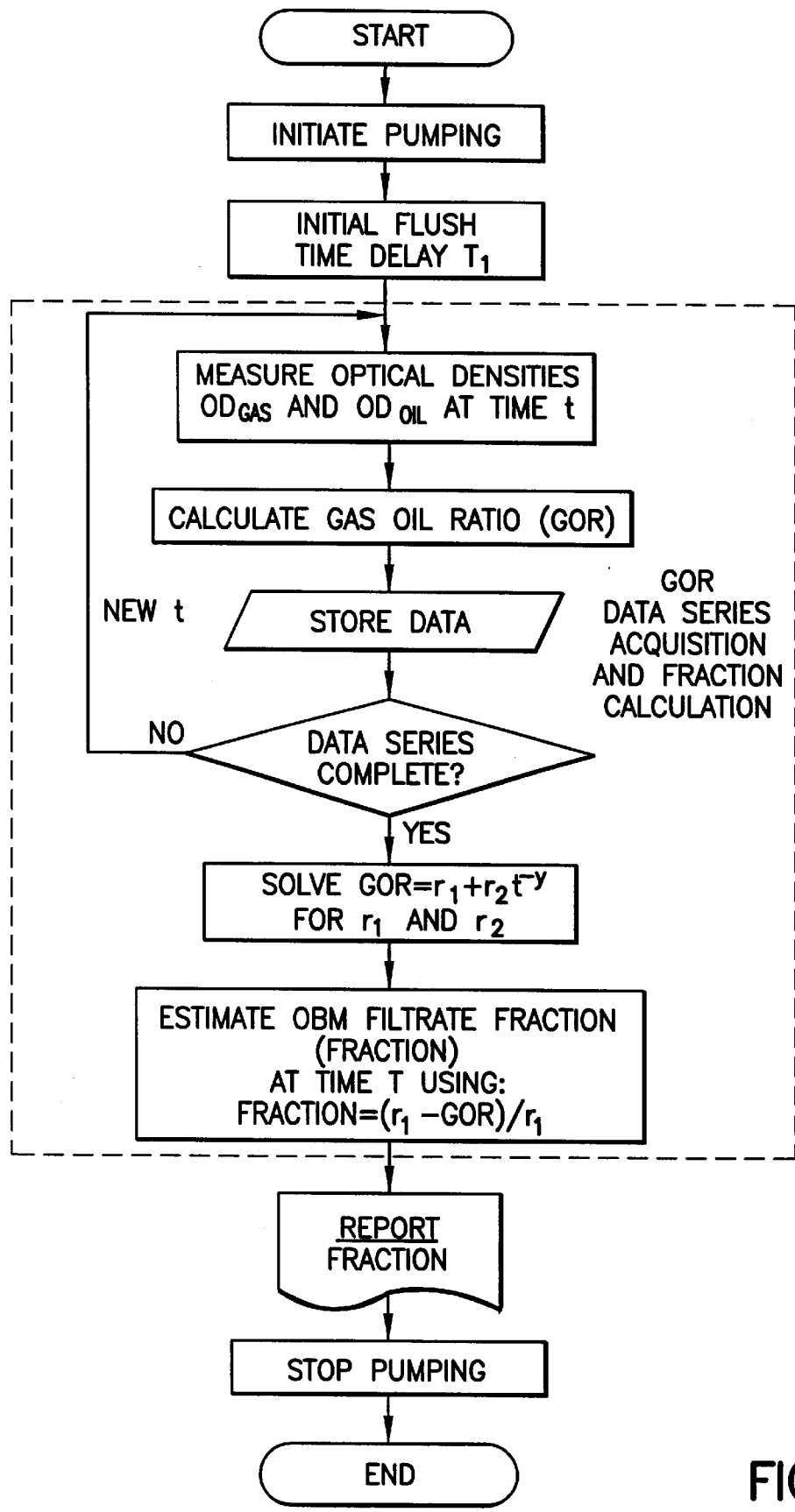
FIG. 9 is a flowchart for a second method of estimating oil based mud filtrate fraction of downhole fluid—using OD measurements and GOR calculations.

A second preferred method of estimating OBM filtrate is illustrated in FIG. 9. The steps of FIG. 9 include making a series of OD measurements, using a calculated GOR to distinguish OBM filtrate from crude oil, Eq. 3, and Eq. 4. Preferably, the form of Eq. 3, used to fit the GOR time evolution curve, is as follows.

$$GOR(t)=r_1+r_2 t^{-y} \qquad \text{Eq. 3}$$

In Eq. 3, $r_1$ is the unknown asymptotic value, $r_2$ is a constant, and y is a selected decay value having a preferred value of approximately 0.5, usually within a range of approximately 0.2 to 0.8, and rarely above 1.0.

After the asymptotic limit has been determined, the OBM contamination filtrate fraction is calculated using Eq. 4.

$$\text{Fraction}=(r_1-GOR)/r_1 \qquad \text{Eq. 4.}$$

In Eq. 4, $r_1$ is a GOR asymptotic value determined by solving Eq. 3 for coefficients, and GOR is a GOR value derived from the series of GOR values.

Determining GOR Corrected for OBM Filtrate Fraction

Figure 10:
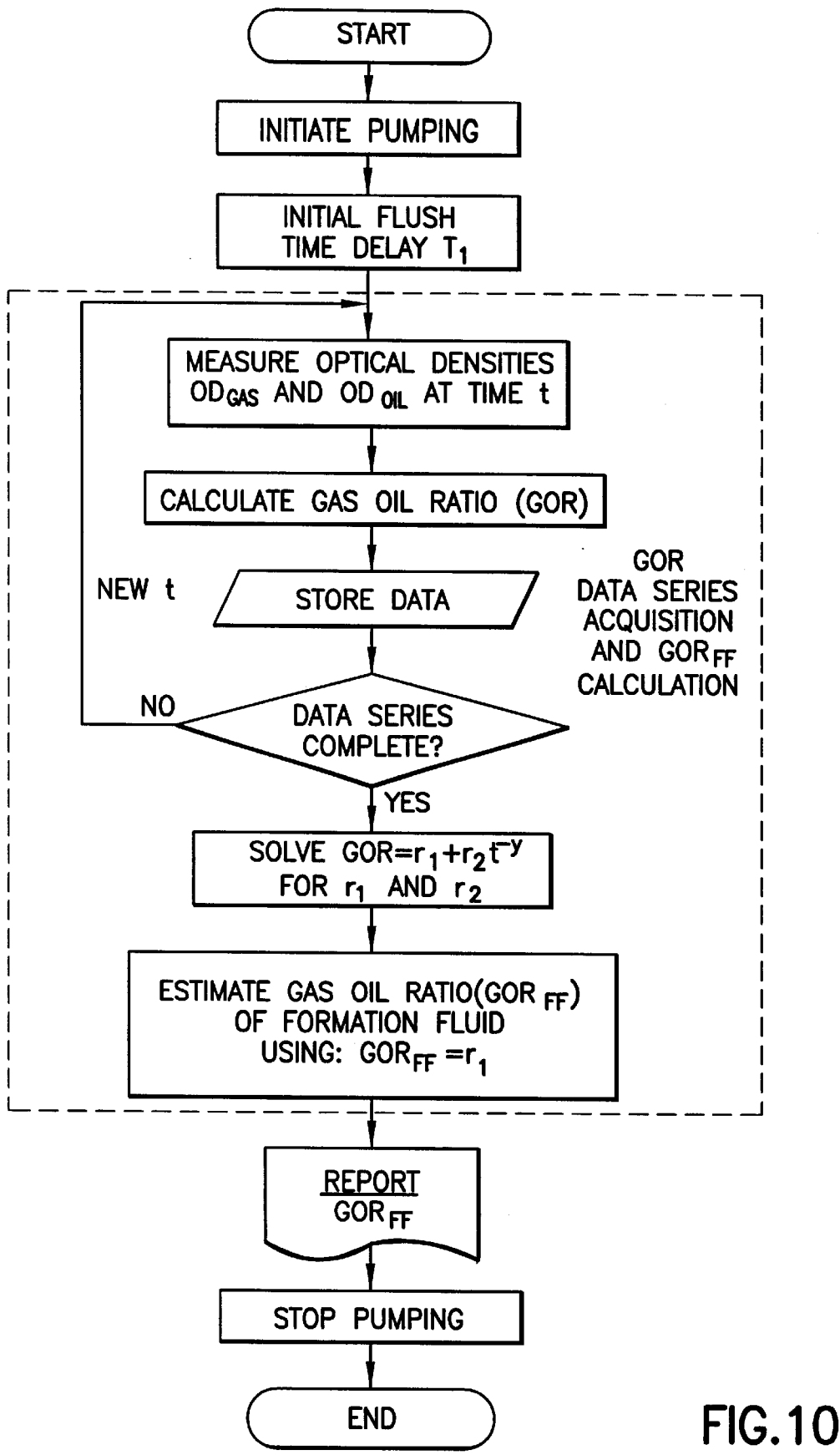
FIG. 10 is a flowchart for estimating GOR of formation fluid, compensated for OBM contamination.

A preferred embodiment of the method for determining gas oil ratio (GOR) of formation fluid from downhole fluid contaminated by OBM filtrate is illustrated in FIG. 10. The method uses a borehole tool having a pump, a flowline, and an optical analyzer. The method includes pumping downhole fluid through the analyzer; illuminating the downhole fluid with light in the visible spectrum and with near infra-red (NIR) light at a wavelength associated with gas; detecting optical absorbance in the visible spectrum to produce a visible spectrum optical density value and NIR absorbance to produce an NIR optical density value; calculating gas oil ratio (GOR) as the ratio of the NIR optical density value to the visible spectrum optical density value; repeating steps a) to d) to produce a series of GOR values at intervals of time; and calculating a GOR asymptotic value from the series of GOR values. Calculating the GOR asymptotic value includes solving a third mathematical function for a coefficient by fitting the series of GOR values to the third mathematical function. The third mathematical function expresses GOR as a function of time, the function having one coefficient representing an unknown GOR asymptotic value, and at least one term which decreases with time. The mathematical function includes $GOR(t)=r_1+r_2 t^{-y}$, in which $r_1$, is the unknown asymptotic value, $r_2$ is a constant, and y is a selected decay value of approximately 0.5 and within the range 0.2 to 0.8.

Determining OD Corrected for OBM Filtrate Fraction

Figure 11:
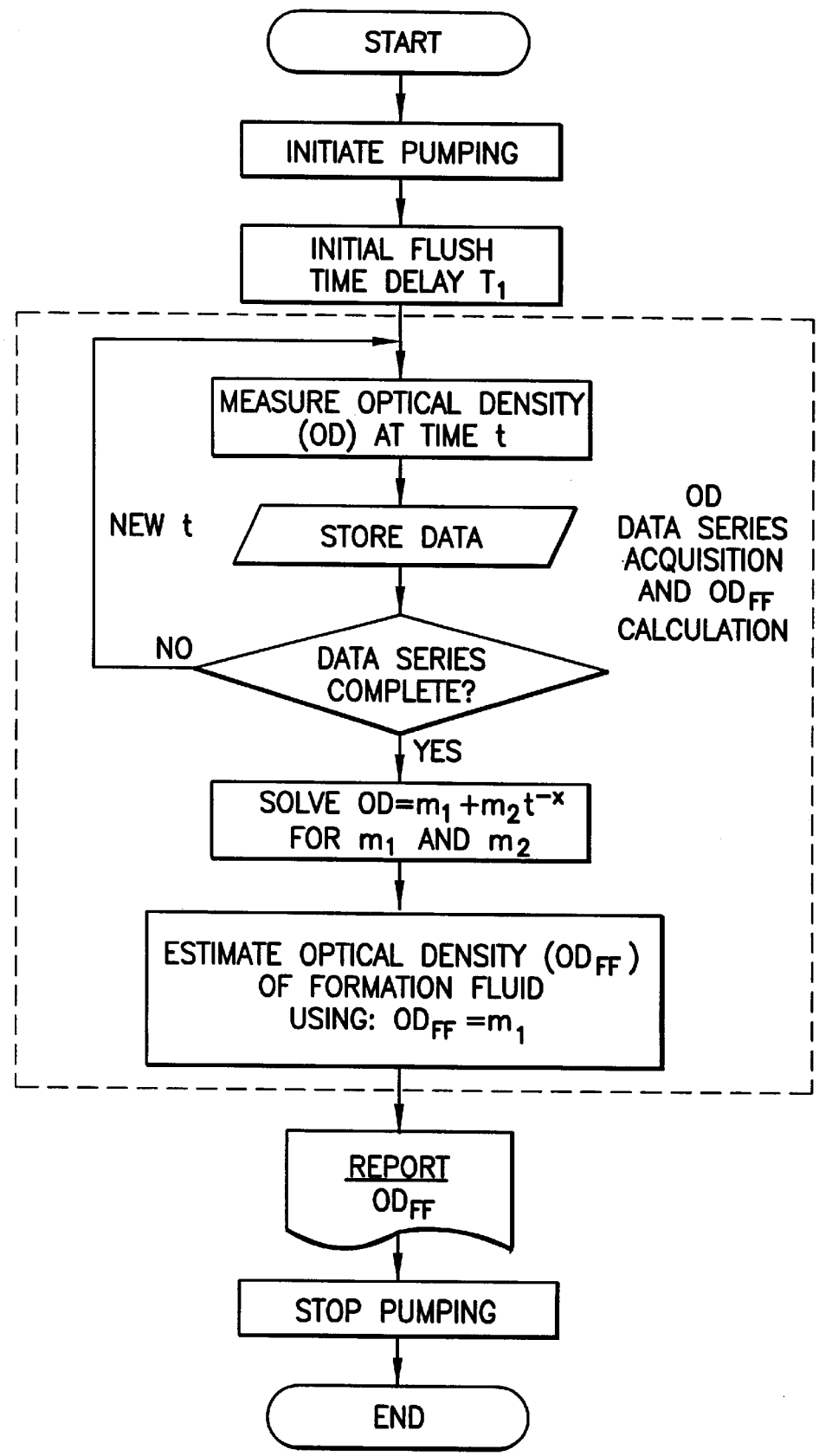
FIG. 11 is a flowchart for estimating OD of formation fluid, coensated for OBM contamination.

A preferred embodiment of the method for determining optical density of formation fluid from downhole fluid contaminated by OBM filtrate is illustrated in FIG. 11. The method uses a borehole tool having a pump, a flowline, and an optical analyzer. The method includes pumping downhole fluid through the analyzer; measuring optical density of downhole fluid to produce a series of optical density values at intervals of time; and calculating an OD asymptotic value indicative of optical density of formation fluid from the series of optical density values. Calculating the OD asymptotic ratio includes solving a first mathematical function for a coefficient by fitting the series of OD values to the first mathematical function. The first mathematical function expresses OD as a function of time, the first mathematical function having one constant coefficient representing an unknown asymptotic value, and at least one term which decreases with time. The first mathematical function includes $OD(t)=m_1+m_2 t^{-x}$, in which $m_1$ is a first constant coefficient representing the unknown OD asymptotic value, $m_2$ is a second constant coefficient, and x is a selected decay value of approximately 0.5 and within the range 0.2 to 0.8.

Circumstances That Make Asymptotic Approach Invalid

The applicants recognized that after pumping begins a period of time is needed to flush the initial high concentration of OBM filtrate out of the system. Under normal circumstances this flushing period is 600 seconds. During the first part of this flushing period the OBM filtrate in the MDT tool is likely to have a high concentration of solids. After this flushing period any significant leakage path for filtrate entry into the MDT tool can result in both continued high concentration of solids and failure of OBM filtrate fraction to trend towards zero—so making the asymptotic approach invalid.

Three interpretation algorithms of the present invention, based on two recognizable artifacts in the OFA log, are used to disqualify asymptotic analysis. The first artifact is a long period of optical scattering. The second artifact is lack of change in the optical density over time. Lack of change in the optical density over time can be tested in two ways—testing for color change and testing for asymptote stability. These three methods of disqualifying the asymptotic analysis can be performed independently and in real time.

Figure 12B:
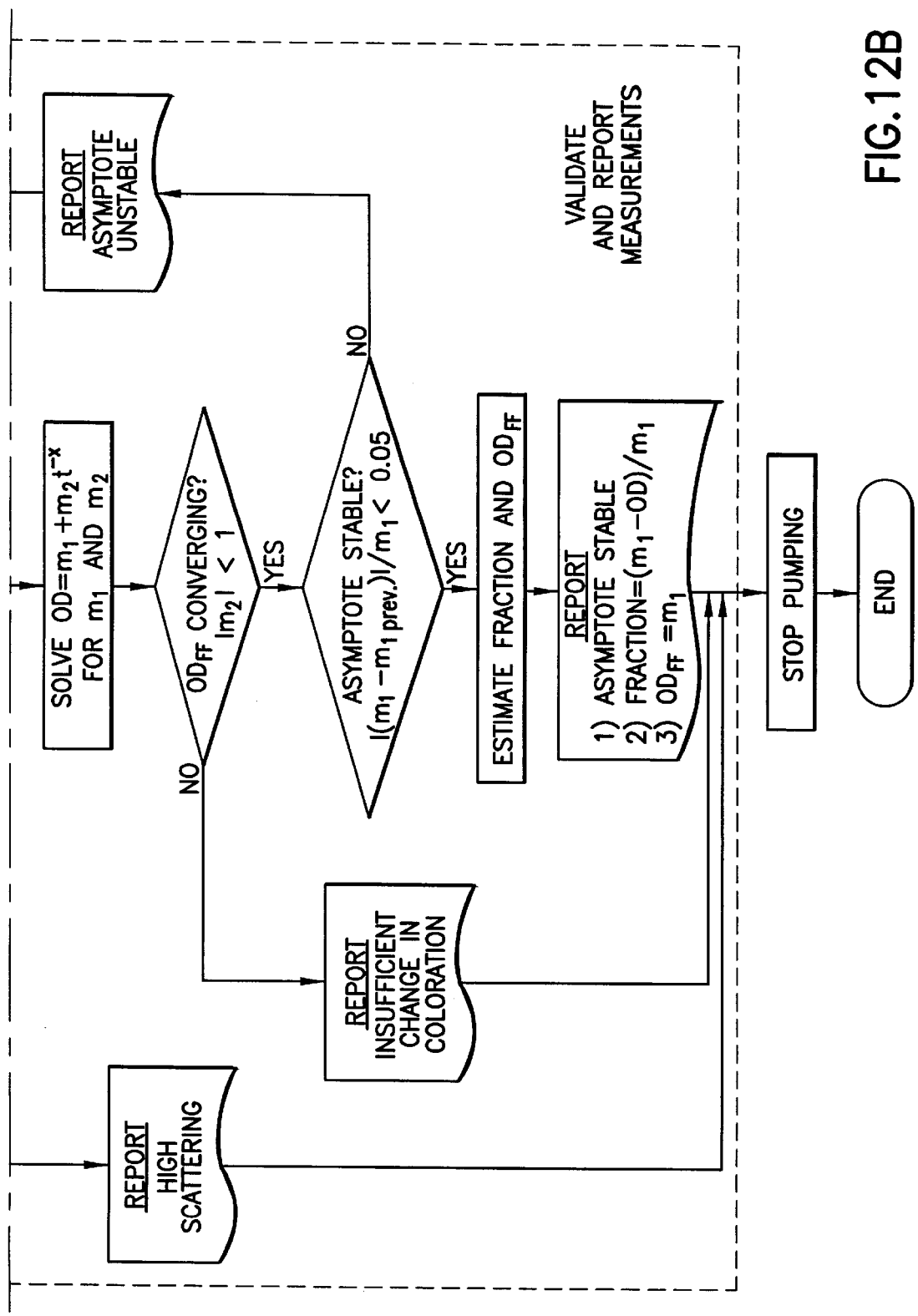
FIG. 12 is a flowchart for validation tests based on scattering convergence and asymptote stability, and outputting reports.

FIG. 12 illustrates the sequencing of validation tests based on scattering, convergence and asymptote stability, and the reporting of OBM filtrate fraction and OD estimates, and validation reports.

Validity Check—Testing for Scattering

A high concentration of solids is seen as optical scattering. A long period of optical scattering most likely indicates optical scattering from mud solids. FIG. 7 shows an example of a log where, after pumpout started, significant optical scattering persisted for 500 seconds and some optical scattering persisted for another 500 seconds. Scattering from mud solids is seen as an increase in optical density on all channels. But the pressure curve (not shown) establishes that these mud solids are not entering the MDT directly from the borehole. Some of these solids are most likely entering from the formation due to pumping fluids out of a formation with an internal mudcake. An internal mudcake provides a leakage path for filtrate entry into the MDT. Thus, the presence of excessive optical scattering at long times after commencement of pumpout could be used to disqualify asymptotic analysis.

Significant leakage path for filtrate entry into the MDT tool can happen when an internal mudcake forms in a formation with large grain sandstone. Also, filtrate can enter the MDT when fluids flow through surface mudcake that is not well formed, and then through a short section of formation (around the packer). When this happens, a steady state may be established with a significant constant fraction of contamination, i.e. no change with time. In the absence of OD change with time, asymptotic analysis would predict no contamination, while in fact there is a significant fraction of contamination.

Optical testing for scattering, as illustrated in FIG. 12, uses light at $1600 \times 10^{-9}$m (1600nm) to measure OD. The test is preferably run after 600 seconds from beginning pumping. The test is:

$$\text{OD Scattering} < 0.02 \qquad \text{Eq. 5}$$

Testing for scattering at wavelength 1600nm is based on the assumption there is no water present in the downhole fluid. This can be verified by spectroscopic analysis using the analyzer in its water-detection mode.

Validity Check—Testing for Lack of OD Change

Lack of change in the optical density over time is used to disqualify asymptotic analysis because it indicates steady state conditions, i.e. lack of convergence to an asymptotic value. What we are looking for is monotonically changing OD values. As seen in the OFA log of FIG. 7, there is very little time-dependent change in optical density on any channel besides that from scattering.

In context of the present invention, if optical density doesn't change, $m_2=0$. As a practical matter, the test is:

$$|m_2| < 1 \qquad \text{Eq. 6}$$

The modulus operation is needed to cover the situation when the value of $m_2$ is negative. The value of $m_2$ is negative when the foundation oil is darker than the OBM filtrate, which it usually is. The use of this test is illustrated in FIG. 12.

Validity Check—Testing for Asymptote Instability

Asymptotic stability is detected as a small monotonic change in estimated OD, the difference between the most recent estimate $m_1$, and the previous estimate $m_{1prev.}$. As illustrated in FIG. 10, the test is:

$$|(m_1 - m_{1prev.})|/m_1 < 0.05 \qquad \text{Eq. 7}$$

Predicting Filtrate Fraction after Further Pumping

Figure 13:
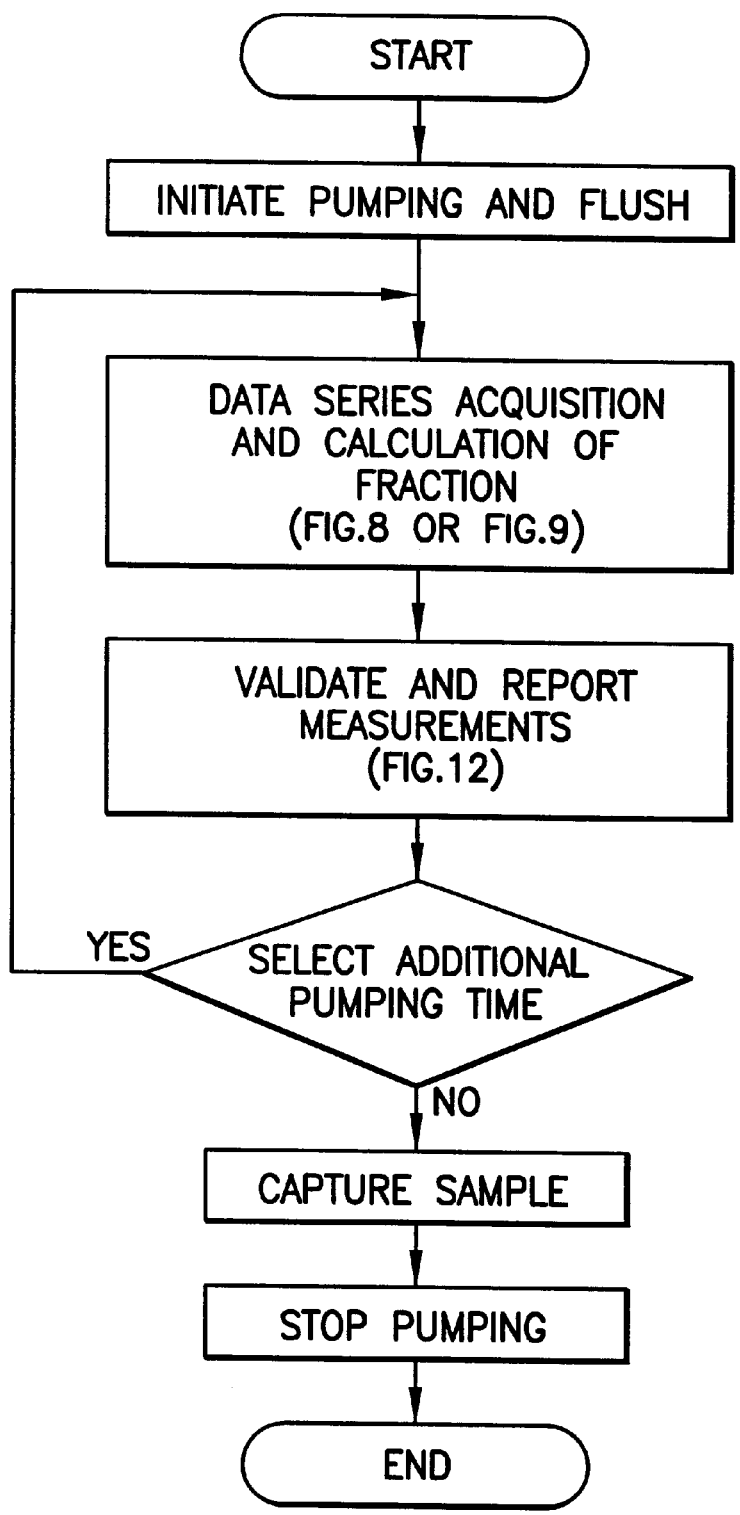
FIG. 13 is a flowchart for the steps leading to sample capture with or without an extended pumping time.
Figure 14:
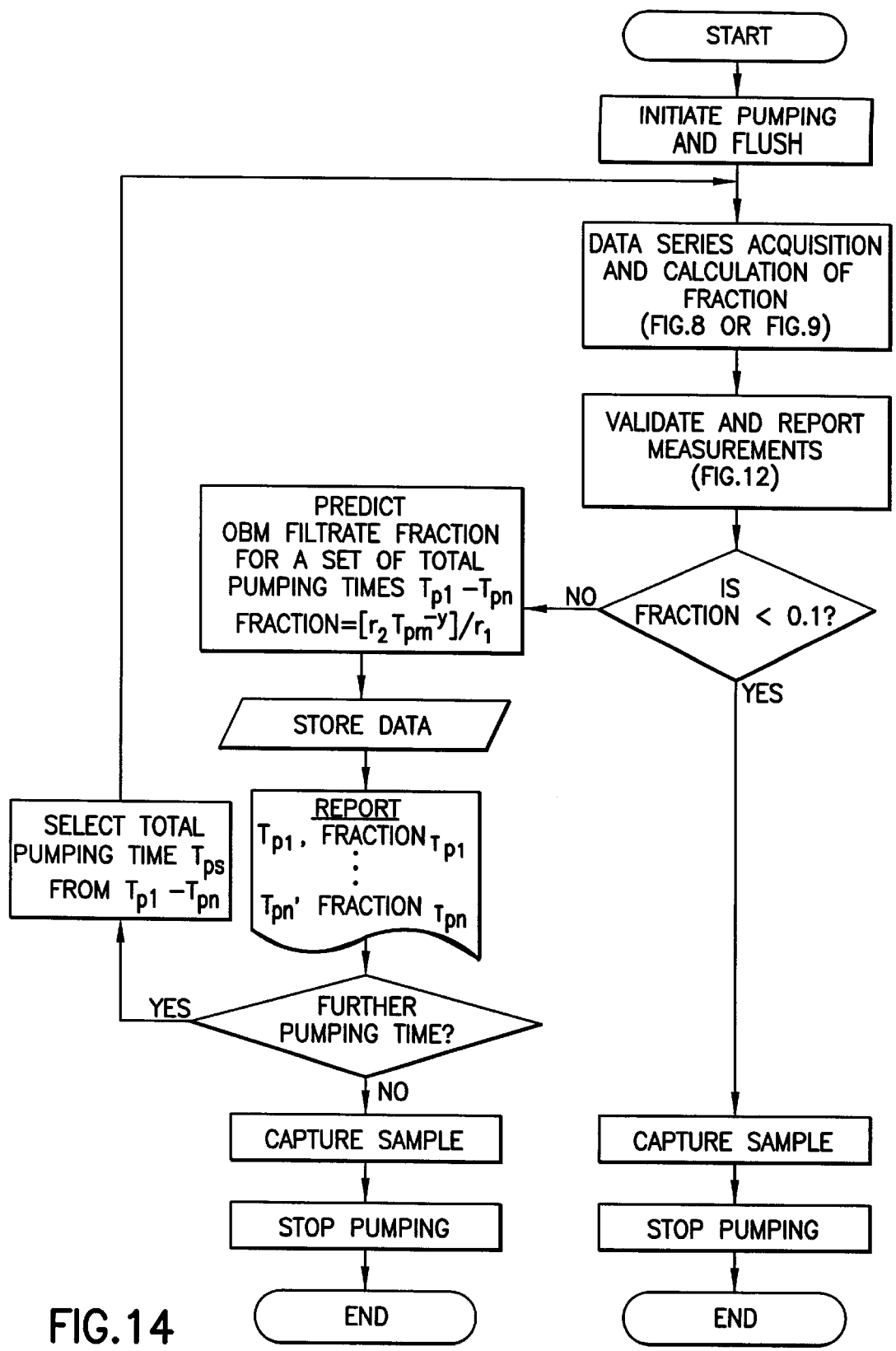
FIG. 14 is a flowchart for the process whereby the operator may be given (a) a prediction of filtrate fraction for extended pumping time and (b) an opportunity to select and initiate an extended pumping time.

The use of further pumping time to achieve better measurements based on a predefined second period of pumping, i.e. a longer flush, is illustrated in FIGS. 13 and 14. FIG. 14 shows sample capture following detection of a stable asymptote (i.e. a monotonic increase in asymptotic values at less than a predetermined rate) and validation that contamination fraction <0.1. The method for initiating sample capture includes an optional method for predicting the reduction of filtrate fraction for a range of extended pumping times. This allows the operator to set an extended pumping time in accordance with the predicted reduction of filtrate fraction and the state of the borehole.

The preferred method for predicting OBM filtrate fraction at the end of the predefined second period of pumping is illustrated in FIG. 14. The method uses a borehole tool having a pump, a flowline, and an optical analyzer, the pump pumping downhole fluid through the analyzer. It includes illuminating the downhole fluid with light in the visible spectrum and with near infra-red (NIR) light at a wavelength associated with gas; detecting optical absorbance in the visible spectrum to produce a visible spectrum optical density value and NIR absorbance to produce NIR optical density value; and repeatedly calculating GOR as the ratio of the NIR optical density value to the visible spectrum optical density value to produce a series of GOR values. It also includes calculating a GOR asymptotic value indicative of predicted OBM filtrate fraction, including solving a third mathematical function for coefficients by fitting the series of GOR values to the first mathematical function, then using at least one of the coefficients in a fifth mathematical function to determine predicted OBM filtrate fraction. In the preferred embodiment, solving a third mathematical function for coefficients includes fitting the series of ratio values to a third mathematical function of the form $GOR(t) = r_1 + r_2 t^{-y}$, in which $r_1$ is the unknown asymptotic value, $r_2$ is a constant, and y is a selected decay value, to solve for $r_1$ and $r_2$; and wherein using at least one of the coefficients in a fifth mathematical function includes solving $$\text{FRACTION} = [r_2 T_{Pm}^{-y}]/r_1 \qquad \text{Eq. 8}$$

for FRACTION, where $T_{Pm}$ is the predefined second period of pumping.

What is claimed is:

1. A method for determining OBM filtrate fraction of downhole fluid, using a borehole tool having a pump, a flowline, and an optical analyzer, the method comprising the steps of:

a) pumping downhole fluid through the analyzer;

b) measuring OD of downhole fluid to produce a series of OD values at intervals of time; and c) calculating an OD asymptotic ratio indicative of OBM filtrate fraction.

2. A method according to claim 1, wherein calculating the OD asymptotic ratio includes solving a first mathematical function for coefficients by fitting the series of OD values to the first mathematical function, then using at least one of the coefficients in a second mathematical function to determine OBM filtrate fraction.

3. A method according to claim 2, wherein the first mathematical function expresses OD as a function of time, the first mathematical function having one coefficient representing an unknown asymptotic value, and at least one term which decreases with time.

4. A method according to claim 3, wherein the first mathematical function includes $OD(t) = m_1 + m_2 t^{-x}$, which $m_1$ is a first coefficient representing the unknown OD asymptotic value, $m_2$ is a second coefficient, and x is a selected decay value.

5. A method according to claim 4, wherein x is approximately 0.5.

6. A method according to claim 4, wherein x is within the range 0.2 to 0.8.

7. A method according to claim 4, wherein the second mathematical function includes Fraction=$(m_1-OD)/m_1$, in which $m_1$, is an OD asymptotic value determined by solving for coefficients, and OD is an OD value derived from the series of OD values.

8. A method according to claim 7, wherein the second mathematical function includes Fraction=$|(m_1-OD)|/m_1$.

9. A method according to claim 4, further comprising the step of testing $m_2$ to verify asymptotic convergence of OD values.

10. A method according to claim 9, further comprising the step of testing for $m_2<1$.

11. A method according to claim 9, further comprising the step of testing for $|m_2|<1$.

12. A method according to claim 4, further comprising the steps of:
repeating steps a) to c) to produce a series of asymptotic values; and
testing the series of asymptotic values for stability.

13. A method according to claim 12, further comprising the step of testing for $(m_1-m_{1prev.})/m_1<0.05$.

14. A method according to claim 12, further comprising the step of testing for $|(m_1-m_{1prev.})|/m_1<0.05$.

15. A method according to claim 1, wherein measuring OD includes illuminating downhole fluid with light of wavelength in the visible spectrum selected in accordance with coloration contrast between formation fluid and OBM filtrate.

16. A method according to claim 15, wherein the wavelength is selected as being the shortest wavelength that yields an OD in the range 0.05 to 2.0.

17. A method according to claim 16, wherein the first wavelength selected is approximately 537 nm.

18. A method according to claim 1, wherein measuring OD includes illuminating downhole fluid with light of wavelength selected in accordance with contrast between the OD of condensate dissolved in the formation fluid and the OD of OBM filtrate.

19. A method according to claim 18, wherein the condensate includes methane.

20. A method according to claim 19, wherein the wavelength is proximate to a methane peak.

21. A method according to claim 20, wherein the wavelength is on a lower wavelength shoulder of a methane peak.

22. A method according to claim 1, further comprising the step of testing for scattering, including testing to determine if OD is less than a predetermined value.

23. A method according to claim 22, wherein testing for scattering includes testing for OD<0.2.

24. A method according to claim 22, wherein testing for scattering includes testing at wavelength 1600 nm.

25. A method for determining OBM filtrate fraction of downhole fluid, using a borehole tool having a pump, a flowline, and an optical analyzer, the method comprising the steps of:
a) pumping downhole fluid through the analyzer;
b) illuminating the downhole fluid with light in the visible spectrum and with near infra-red (NIR) light at a wavelength associated with gas;
c) detecting optical absorbance in the visible spectrum to produce a visible spectrum optical density value and NIR absorbance to produce an NIR optical density value;
d) calculating GOR as the ratio of the NIR optical density value to the visible spectrum optical density value;
e) repeating steps a) to d) to produce a series of GOR values at intervals of time; and
f) calculating a GOR asymptotic ratio indicative of OBM filtrate fraction.

26. A method according to claim 25, wherein calculating the GOR asymptotic ratio includes solving a third mathematical function for its coefficients by fitting the series of OD values to the third mathematical function, then using at least one of the coefficients in a fourth mathematical function to determine OBM filtrate fraction.

27. A method according to claim 26, wherein the third mathematical function expresses GOR as a function of time, the third mathematical function having one constant coefficient representing an unknown asymptotic value, and at least one term which decreases with time.

28. A method according to claim 27, wherein the third mathematical function includes $GOR(t)=r_1+r_2t^{-y}$, in which $r_1$ is a first constant coefficient representing the unknown GOR asymptotic value, $r_2$ is a second constant coefficient, and y is a selected decay value.

29. A method according to claim 28, wherein y is approximately 0.5.

30. A method according to claim 28, wherein y is within the range 0.2 to 0.8.

31. A method according to claim 26, wherein the fourth mathematical function includes Fraction=$(r_1-OD)/r_1$, in which $r_1$ is the asymptotic value determined by solving for coefficients, and OD is an OD value derived from the series of OD values.

32. A method for determining GOR of formation fluid, from downhole fluid contaminated by OBM filtrate, using a borehole tool having a pump, a flowline, and an optical analyzer, the method comprising the steps of:
a) pumping downhole fluid through the analyzer;
b) illuminating the downhole fluid with light in the visible spectrum and with near infra-red (NIR) light at a wavelength associated with gas;
c) detecting optical absorbance in the visible spectrum to produce a visible spectrum optical density value and NIR absorbance to produce an NIR optical density value;
d) calculating GOR as the ratio of the NIR optical density value to the visible spectrum optical density value;
e) repeating steps a) to d) to produce a series of GOR values at intervals of time; and
f) calculating a GOR asymptotic value from the series of GOR values.

33. A method according to claim 32, wherein calculating the GOR asymptotic value includes solving a third mathematical function for a coefficient by fitting the series of GOR values to the third mathematical function.

34. A method according to claim 33, wherein the third mathematical function expresses GOR as a function of time, the function having one coefficient representing an unknown GOR asymptotic value, and at least one term which decreases with time.

35. A method according to claim 34, wherein the mathematical function includes $GOR(t)=r_1+r_2t^{-Y}$, in which $r_1$ is the unknown asymptotic value, $r_2$ is a constant, and y is a selected decay value.

36. A method according to claim 35, wherein y is approximately 0.5.

37. A method according to claim 35, wherein y is within the range 0.2 to 0.8.

38. A method for determining optical density of formation fluid, from downhole fluid contaminated by OBM filtrate, using a borehole tool having a pump, a flowline, and an optical analyzer, the method comprising the steps of:
  a) pumping downhole fluid through the analyzer;
  b) measuring optical density of downhole fluid to produce a series of optical density values at intervals of time; and
  c) calculating an OD asymptotic value indicative of optical density of formation fluid from the series of optical density values.

39. A method according to claim 38, wherein calculating the OD asymptotic ratio includes solving a first mathematical function for a coefficient by fitting the series of OD values to the first mathematical function.

40. A method according to claim 39, wherein the first mathematical function expresses OD as a function of time, the first mathematical function having one constant coefficient representing an unknown asymptotic value, and at least one term which decreases with time.

41. A method according to claim 40, wherein the first mathematical function includes $OD(t)=m_1+m_2 t^{-x}$, in which $m_1$ is a first constant coefficient representing the unknown OD asymptotic value, $m_2$ is a second constant coefficient, and x is a selected decay value.

42. A method according to claim 41, wherein x is approximately 0.5.

43. A method according to claim 41, wherein x is within the range 0.2 to 0.8.

44. A method for validating initiation of sample capture of downhole fluid, using a borehole tool having a pump, a flowline, an optical analyzer, and means for capturing a sample, the method comprising the steps of:
  a) pumping downhole fluid through the analyzer;
  b) measuring OD of downhole fluid to produce a series of OD values at intervals of time;
  c) testing for scattering; and
  d) initiating sample capture if scattering is less than a predetermined value.

45. A method according to claim 44, wherein the predetermined value is 0.2.

46. A method according to claim 44, wherein measuring OD of downhole fluid includes illuminating the downhole fluid at a wavelength of approximately 1600 nm.

47. A method for validating initiation of sample capture of downhole fluid, using a borehole tool having a pump, a flowline, an optical analyzer, and means for capturing a sample, the method comprising the steps of:
  a) pumping downhole fluid through the analyzer;
  b) measuring OD of downhole fluid produce a series of optical density values at intervals of time;
  c) calculating an asymptotic value indicative of optical density of formation fluid from the series of optical density values;
  d) repeating steps a) through c) to produce a series of asymptotic values; and
  e) initiating sample capture if asymptotic values are monotonicaly changing at less than a predetermined rate.

48. A method for predicting OBM filtrate fraction of downhole fluid after a predefined second period of pumping, using a borehole tool having a pump, a flowline, and an optical analyzer, the method comprising the steps of:
  a) pumping downhole fluid through the analyzer;
  b) illuminating the downhole fluid with light in the visible spectrum and with near infra-red (NIR) light at a wavelength associated with gas;
  c) detecting optical absorbance in the visible spectrum to produce a visible spectrum optical density value and NIR absorbance to produce NIR optical density value;
  d) calculating GOR as the ratio of the NIR optical density value to the visible spectrum optical density value;
  e) repeating steps a) to d) during a first period of pumping to produce a series of GOR values at intervals of time; and
  f) calculating a GOR asymptotic value indicative of predicted OBM filtrate fraction, including solving a third mathematical function for coefficients by fitting the series of GOR values to the first mathematical function, then using at least one of the coefficients in a fifth mathematical function to determine predicted OBM filtrate fraction.

49. A method according to claim 48, wherein solving a third mathematical function for coefficients includes fitting the series of ratio values to a third mathematical function of the form $GOR(t)=r_1+r_2 t^{-y}$, in which $r_1$ is the unknown asymptotic value, $r_2$ is a constant, and y is a selected decay value, to solve for $r_1$ and $r_2$; and
  wherein using at least one of the coefficients in a fifth mathematical function includes solving equation $FRACTION=(r_2 T_{Pm}^{-y})/r_1)$, where $T_{Pm}$ is the predefined second period of pumping.

50. A borehole apparatus, comprising:
  a borehole tool including a flowline with an optical cell, a pump coupled to the flowline for pumping downhole fluid through the cell, and an analyzer optically coupled to the cell and configured to produce OD values; and
  control means, coupled to the borehole tool, including means for accepting OD values from the borehole tool and calculating from the OD values an asymptotic value.

51. A borehole apparatus according to claim 50, wherein the asymptotic value is an OD asymptotic value indicative of OBM filtrate fraction.

52. A borehole apparatus according to claim 50, wherein the asymptotic value is a GOR asymptotic ratio indicative of OBM filtrate fraction.

53. A borehole apparatus according to claim 50, wherein the asymptotic value is a GOR asymptotic value indicative of GOR corrected for OBM filtrate fraction.

54. A borehole apparatus according to claim 50, wherein the asymptotic value is an OD asymptotic value indicative of OD corrected for OBM filtrate fraction.

55. A borehole apparatus according to claim 50, wherein the control means further includes means for testing OD values to validate measurement by confirming absence of scattering.

56. A borehole apparatus according to claim 50, wherein the control means further includes means for testing OD values to validate measurement by confirming asymptotic convergence.

57. A borehole apparatus according to claim 50, wherein the control means further includes means for testing OD values to validate measurement by confirming stable asymptote.

58. A borehole apparatus according to claim 50, wherein the asymptotic value is an OD asymptotic value indicative of OBM filtrate fraction associated with a selected additional pumping time.

59. A computer usable medium having computer readable program code thereon, the medium adapted for use with borehole apparatus, the program code including code structured to (a) accept a series of OD values;

(b) calculate from the OD values an asymptotic value; and (c) calculate from the asymptotic value an OBM filtrate fraction.

60. A computer usable medium having computer readable program code thereon, the medium adapted for use with borehole apparatus, the program code including code structured to (a) accept a series of OD values;

(b) calculate from the OD values an asymptotic value; and (c) calculate from the asymptotic value a GOR of formation fluid.

61. A computer usable medium having computer readable program code thereon, the medium adapted for use with borehole apparatus, the program code including code structured to (a) accept a series of OD values and a selected additional pumping time;

(b) calculate from the OD values and the selected additional pumping time an asymptotic value; and (c) calculate from the asymptotic value an OBM filtrate fraction associated with the selected additional pumping time.

* * * * *

(12) EX PARTE REEXAMINATION CERTIFICATE (5455th)
United States Patent
Schroer et al.

(10) Number: US 6,274,865 C1
(45) Certificate Issued: Jul. 18, 2006

(54) ANALYSIS OF DOWNHOLE OBM-CONTAMINATED FORMATION FLUID

(75) Inventors: Jon J. Schroer, Bear, DE (US); Oliver C. Mullins, Ridgefield, CT (US)

(73) Assignee: Schlumberger Technology Corporation, Ridgefield, CT (US)

Reexamination Request:
No. 90/006,748, Aug. 14, 2003

Reexamination Certificate for:
Patent No.: 6,274,865
Issued: Aug. 14, 2001
Appl. No.: 09/255,999
Filed: Feb. 23, 1999

(51) Int. Cl.
*G01V 8/02* (2006.01)

(52) U.S. Cl. .................. 250/269.1; 250/255; 250/256
(58) Field of Classification Search .............. 250/269.1, 250/255, 256, 262, 261
See application file for complete search history.

(56) References Cited

U.S. PATENT DOCUMENTS

| | | | | |
|---|---|---|---|---|
| 3,780,575 | A | * 12/1973 | Urbanosky | 73/152.26 |
| 3,859,851 | A | * 1/1975 | Urbanosky | 73/152.24 |
| 4,860,581 | A | * 8/1989 | Zimmerman et al. | 73/152.26 |
| 4,936,139 | A | * 6/1990 | Zimmerman et al. | 73/152.26 |
| 4,994,671 | A | * 2/1991 | Safinya et al. | 250/255 |
| 5,167,149 | A | * 12/1992 | Mullins et al. | 73/152.42 |
| 5,201,220 | A | * 4/1993 | Mullins et al. | 73/152.42 |
| 5,247,830 | A | * 9/1993 | Goode | 73/152.51 |
| 5,266,800 | A | * 11/1993 | Mullins | 250/256 |
| 5,331,156 | A | * 7/1994 | Hines et al. | 250/256 |
| 5,859,430 | A | * 1/1999 | Mullins et al. | 250/255 |
| 6,178,815 | B1 | * 1/2001 | Felling et al. | 73/152.19 |

OTHER PUBLICATIONS

Mullins et al. (Real time Determination of Filtrate Contamination During Open Wireline Sampling by Optical Spectroscopy, Oct. 2000).*

Mullins et al. "Determination of Producible Hydrocarbon Type and Oil Quality in Wells Drilled with Synthetic Oil-Based Muds" (presented Oct. 1997), SPE 39093 (pp. 353–368).*

Hammond "One– and Two–Phase Flow During Fluid Sampling by a Wireline Tool" (1991), Transport in Porous Media 6 (pp. 299–330).*

Fetkovich et al. "Useful Concepts for Decline–Curve Forecasting, Reserve Estimation and Analysis" (Feb. 1996), SPE Reservoir Engineering (pp. 13–22).*

Felling et al. "Characterization of In–Situ Fluid Responses by Use of Optical Fluid Analysis" (Aug. 1998), SPE Reservoir Evaluation and Engineering (pp. 297–302).*

* cited by examiner

*Primary Examiner*—Albert Gagliardi

(57) ABSTRACT

A method and apparatus is provided for determining OBM filtrate fraction in a downhole fluid sample. One embodiment of the method is used when there is significant difference between the coloration of formation fluid and the coloration of OBM filtrate. Another is used when there is little or no difference between the coloration of formation fluid and the coloration of OBM filtrate. Another determines GOR of formation fluid corrected for OBM filtrate contamination. Another determines OD of formation fluid corrected for OBM filtrate contamination. Another determines conditions that would render optical density measurements invalid and sample capture premature. Another predicts the reduction of filtrate fraction for a specific extended pumping time. Another initiates sample capture when computed contamination fraction exhibits stable asymptotic convergence.

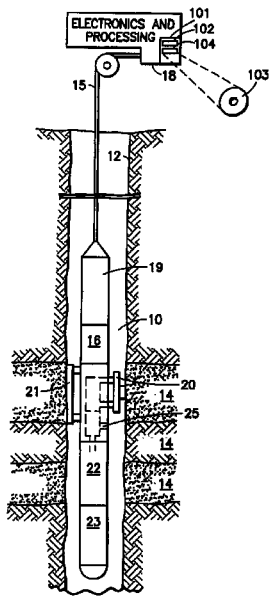

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–43 and 47–61 is confirmed.

Claims 44–46 are cancelled.

\* \* \* \* \*